United States Patent
Nifant'ev et al.

(10) Patent No.: US 6,451,724 B1
(45) Date of Patent: Sep. 17, 2002

(54) METALLOCENES AND CATALYSTS FOR OLEFIN-POLYMERISATION

(75) Inventors: Ilya E. Nifant'ev; Vladimir V. Bagrov, both of Moscow (RU)

(73) Assignee: Basell Technology Company BV, Hoofddorp (NL)

(*) Notice: Subject to any disclaimer, the term of this patent is extended or adjusted under 35 U.S.C. 154(b) by 0 days.

(21) Appl. No.: 09/341,438

(22) PCT Filed: Nov. 4, 1998

(86) PCT No.: PCT/EP98/07034

§ 371 (c)(1),
(2), (4) Date: Jul. 8, 1999

(87) PCT Pub. No.: WO99/24446

PCT Pub. Date: May 20, 1999

(30) Foreign Application Priority Data

Nov. 12, 1997 (EP) .............................. 97119778

(51) Int. Cl.$^7$ .......................... C08F 17/00; C08F 7/08; C08F 4/44; B01J 31/38

(52) U.S. Cl. ................. 502/103; 526/127; 526/160; 526/161; 526/943; 502/152; 502/155; 556/11; 556/12; 556/23; 556/53

(58) Field of Search .................. 526/160, 943, 526/161, 127; 502/152; 556/52

(56) References Cited

U.S. PATENT DOCUMENTS 6,232,260 B1 * 5/2001 Nagy et al. ............. 502/155

FOREIGN PATENT DOCUMENTS

| EP | 0 035 242 A1 | 9/1981 |
|---|---|---|
| EP | 0 129 368 A1 | 12/1984 |
| EP | 0 604 908 A2 * | 4/1994 |
| EP | 0 604 908 A2 | 7/1994 |
| WO | 95/27717 | 10/1995 |
| WO | 98/22486 | 5/1998 |
| WO | 98/37106 | 8/1998 |

OTHER PUBLICATIONS

Derwent abstract of EP 035 242, Keminsky et al., Sep. 9, 1951.

* cited by examiner

*Primary Examiner*—David W. Wu
*Assistant Examiner*—R. Harlan
(74) *Attorney, Agent, or Firm*—Bryan Cave LLP

(57) ABSTRACT

A class of metallocenes of formula (I): $(ZR^1{}_m)_n(Cp)(A)_r ML_pL'_q$ (I) wherein $(ZR^1{}_m)_n$ is a divalent group bridging Cp and A, Cp is a heterocyclic cyclopentadienyl group of formula (II) or (II'), wherein one of X or Y is a single bond, the other being an heteroatom; $R^2$ and $R^3$ are hydrogen, halogen or a hydrocarbon radical, optionally containing heteroatoms; $R^4$ is halogen or an hydrocarbon radical, optionally containing heteroatoms; the group A is a cyclopentadienyl derivative or is equal to Cp; M is Ti, Zr or Hf; m is 1 or 2; n ranges from 0 to 4; r is 0 or 1; p and q range from 0 to 3; and a ranges from 0 to 4. Moreover, are disclosed catalyst systems containing these metallocenes, useful in the polymerization of olefins.

16 Claims, No Drawings

METALLOCENES AND CATALYSTS FOR OLEFIN-POLYMERISATION

FIELD OF THE INVENTION

The present invention relates to a new class of metallocenes, to a catalyst for the polymerization of olefins comprising said metallocenes and to a processes for the polymerization of olefins carried out in the presence of said catalyst. The invention also relates to a novel class of ligands useful as intermediates in the synthesis of said metallocenes.

PRIOR ART DISCLOSURE

Many metallocene compounds known in the state of the art are active as catalyst components in olefin polymerization reactions, in association with suitable cocatalysts, such as alumoxanes or aluminum derivatives. For instance, European patent application EP 0 035 242 discloses a process for the polymerization of ethylene and propylene in the presence of a catalyst system comprising a cyclopentadienyl complex of a transition metal.

European patent application EP 0 129 368 discloses a catalyst system for the polymerization of olefins comprising a bis-cyclopentadienyl coordination complex with a transition metal, wherein the two cyclopentadienyl groups may be linked by a bridging group. Said bridging group is generally a divalent radical containing one or more carbon atoms (such as an ethylene group) or containing heteroatoms (such as a dimethylsilanediyl group).

Bridged metallocene compounds wherein the cyclopentadienyl residue is condensed to one or more aromatic or non aromatic ring are known in the state of the art; for example, European patent application EP 0 604 908 discloses a class of catalysts useful in the polymerization of olefins, in particular in the preparation of high molecular weight atactic polypropylene, comprising a bis-fluorenyl compound bridged by means of a one atom bridge. International application WO 95/27717, in the name of the same Applicant, discloses a class of bridged and unbridged metallocenes useful as catalytic components in the polymerization of ethylene and/or propylene, characterized by the fact that the cyclopentadienyl ligands have two or four adjacent substituents forming one or two alkylenic cycles of 4–8 carbon atoms; examples of these metallocenes are bis(1,2-cyclotetramethyleneinden-1-yl) titaniumdichloride, dimethylsilanediyl-bis(2,3-cyclotetramethylene-inden-1-yl)-zirconium dichloride, dimethylsilanediyl-bis(2,3-octahydrofluorenyl)-zirconium dichloride and isopropyliden-(cyclopentadienyl)(2,3-cyclotetramethyleneinden-1-yl)zirconium dichloride.

The international patent application WO 98/22486, in the name of the same Applicant, describes bridged or unbridged metallocenes comprising at least a coordinating group containing a six 7 electron central radical, directly coordinating a transition metal atom, to which are associated one or more radicals containing at least one non carbon atom selected from B, N, O, Al, Si, P, S, Ga, Ge, As, Se, In, Sn, Sb and Te. Said metallocenes are useful as catalyst components for the production of polyethylene and polypropylene.

The international patent application WO 98/37106 describes a polymerization catalyst system comprising a catalytic complex formed by activating a transition metal compound which comprises a group 13, 15 or 16 heterocyclic fused cyclopentadienide ligand and a metal selected from the group consisting of Group 3–9 and 10 metals; said heterocyclic fused cyclopentadienide ligand preferably contains, as endocyclic heteroatoms, one or more B, N, P, O or S atoms.

SUMMARY OF THE INVENTION

The Applicant has now unexpectedly found new metallocene compounds useful as catalyst components in the polymerization of olefins. It is an object of the present invention a class of bridged or unbridged metallocenes of formula (I):

$$(ZR^1{}_m)_n(Cp)(A)_rML_pL'_q \quad (I)$$

wherein $(ZR^{1m})_n$ is a divalent group bridging Cp and A, Z being C, Si, Ge, N or P, and the $R^1$ groups, equal or different from each other, being H or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups;

Cp is a heterocyclic cyclopentadienyl group of formula (II) or (II'):

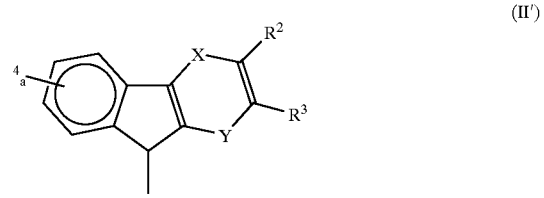

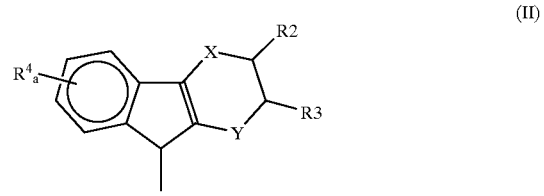

wherein one of X or Y is a single bond, the other being O, S, $NR^6$ or $PR^6$, $R^6$ being hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups, optionally containing one or more atoms belonging to groups 13–16 of the Periodic Table of the Elements (new IUPAC notation), such as B, Al, Si, Ge, N, P, O and S atoms;

$R^2$ and $R^3$, equal or different from each other, are selected from the group consisting of hydrogen, halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl, —$OR^6$, —$OCOR^6$, —$SR^6$, $PR^6{}_2$, wherein $R^6$ has the meaning reported above; or $R^2$ and $R^3$ form together a condensed $C_5$–$C_7$ ring, saturated, unsaturated or aromatic, optionally containing one or more atoms belonging to groups 13–16 of the Periodic Table of the Elements (new IUPAC notation), such as B, Al, Si, Ge, N, P, O and S atoms;

the substituents $R^4$, equal or different from each other, are selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl, —$OR^6$, —$OCOR^6$, —$SR^6$, —$NR^6{}_2$ and —$PR^6{}_2$, wherein $R^6$ has the meaning reported above, optionally containing one or more atoms belonging to groups 13–16 of the Periodic Table of the Elements (new IUPAC notation), such as B, Al, Si, Ge, N, P, O and S atoms;

a is an integer ranging from 0 to 4;

Cp can be a partially hydrogenated derivative of the heterocyclic cyclopentadienyl group of formula (II) or (II') reported above;

A is a substituted or unsubstituted cyclopentadienyl, a group —NR$^6$, R$^6$ having the meaning reported above, or corresponds to (II) or (II'), or to a partially hydrogenated derivative of (II) or (II');

M is a transition metal belonging to group 3, 4, 5, 6 or to the lanthanide or actinide groups of the Periodic Table of the Elements (IUPAC version); the substituents L, same or different from each other, are monoanionic sigma ligands selected from the group consisting of hydrogen, halogen, —R$^6$, —OR$^6$, —OCOR$^6$, —OSO$_2$CF$_3$, —SR$^6$, —NR$^6_2$ and —PR$^6_2$, wherein the groups R$^6$, same or different from each other, have the meaning reported above and optionally contain Si or Ge atoms;

the substituents L', same or different from each other, are coordinating molecules, such as Lewis bases;

m is 1 or 2, and more specifically it is 1 when Z is N or P, and it is 2 when Z is C, Si or Ge;

n is an integer ranging from 0 to 4; r is 0 or 1; n is 0 when r is 0;

p and q are integers ranging from 0 to 3, p being equal to the valence of the metal M minus 2 when r=1, and minus 1 when r=0, and p+q being ≦3.

The present invention further concerns a new class of bridged ligands of formula (IV):

$$(ZR^1_m)_n(CP)(A) \quad\quad (IV)$$

wherein Cp, A, $(ZR^1_m)_n$, Z, R$^1$ and m have the meaning reported above and n is an integer ranging from 1 to 4, particularly useful as intermediates in the preparation of the above metallocenes.

Another object of the present invention is a catalyst for the polymerization of olefins comprising said metallocenes and their use in the polymerization of olefins, particularly in the production of homo and copolymers of ethylene.

DETAILED DESCRIPTION OF THE INVENTION

In the metallocenes of formula (I), particularly suitable as catalytic components in the polymerization of olefins, the divalent bridge $(ZR^1_m)_n$ is preferably selected from the group consisting of CR$^1_2$, SiR$^1_2$, GeR$^1_2$, NR$^1$, PR$^1$ and (CR$^1_2$)$_2$, R$^1$ having the meaning reported above. More preferably, said divalent bridge is Si(CH$_3$)$_2$, SiPh$_2$, CH$_2$, (CH$_2$)$_2$ or C(CH$_3$)$_2$; even more preferably, it is Si(CH$_3$)$_2$ or CH$_2$.

m is 1 or 2; n ranges from 0 to 4 and, when n>1, the atoms Z can be the same or different from each other, such as in the divalent bridges —CH$_2$—Si(CH$_3$)$_2$—, —CH$_2$—O— and —CH$_2$—S—.

According to a preferred subclass of metallocenes of the present invention, in the heterocyclic cyclopentadienyl of formula (I) or (II'), R$^2$ and R$^3$ form together a condensed benzene ring, Cp corresponding to formula (III):

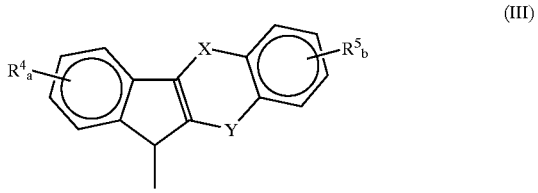

(III)

wherein the substituents R$^5$, equal or different from each other, are selected from the group consisting of halogen, linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl, C$_7$–C$_{20}$ arylalkyl, —OR$^6$, —OCOR$^6$, —SR$^6$, —NR$^6_2$ and —PR$^6_2$, wherein R$^6$ has the meaning reported above; a is an integer ranging from 0 to 4; b is an integer ranging from 0 to 4; the other variables have the meaning reported above.

Cp is preferably 5,10-dihydroindeno[1,2-b]indol-10-yl, N-methyl-5,10-dihydroindeno[1,2-b]indol-10-yl or N-phenyl-5,10-dihydroindeno[1,2-b]indol-10yl, corresponding to formula (III) wherein X is NR$^6$, R$^6$ being hydrogen, methyl and phenyl respectively, and Y is single bond.

Furthermore, Cp can be 5,6-dihydroindeno[2,1-b]indol-6-yl, N-methyl-5,6-dihydroindeno[2,1-b]indol-6-yl, N-allyl-5,6-dihydroindeno[2,1-b]indol-6-yl or N-phenyl- 5,6-dihydroindeno[2,1-b]indol-6-yl, corresponding to formula (III), wherein X is a single bond and Y is NR$^6$, R$^6$ being hydrogen, methyl, allyl and phenyl respectively.

The group A is preferably a cyclopentadienyl residue substituted with at least a substituent selected from the group consisting of H, linear or branched, saturated or unsaturated C$_1$–C$_{10}$ alkyl, C$_6$–C$_{20}$ cycloalkyl, C$_6$–C$_{20}$ aryl, C$_7$–C$_{20}$ alkylaryl and C$_7$–C$_{20}$ arylalkyl radicals. preferably, A is cyclopentadienyl, 4-butyl-cyclopentadienyl, 4-adamantyl-cyclopentadienyl, indenyl, tetrahydroindenyl or fluorenyl. According to a preferred embodiment of the invention, A is equal to Cp.

r can be 0 or 1; when r=0, then n=0.

M is preferably Ti, Zr or Hf, and more preferably Zr.

The substituents L are preferably halogen atoms or R$^6$ groups, R$^6$ being defined as reported above; more preferably the substituents L are Cl or CH$_3$.

p and q are integers ranging from 0 to 3, p being equal to the valence of the metal M minus 2 when r=1, and minus 1 when r=0, and p+q being ≦3;

An advantageous class of the metallocenes according to the present invention correspond to formula (1), wherein n=0 and r=1, i.e. Cp and A groups are not linked to each other by a bridging divalent residue. Non limitative examples of said class are:

bis(N-methyl-5,10-dihydroindeno[1,2-b]indol-10-yl) titanium dichloride;

bis(N-methyl-5,10-dihydroindeno[1,2-b]indol-10-yl) zirconium dichloride;

bis(N-methyl-5,10-dihydroindeno[1,2-b]indol-10-yl) hafnium dichloride;

bis(N-phenyl-5,10-dihydroindeno[1,2-b]indol-10-yl) titanium dichloride;

bis(N-phenyl-5,10-dihydroindeno[1,2-b]indol-10-yl) zirconium dichloride;

bis(N-phenyl-5,10-dihydroindeno[1,2-b]indol-10-yl) hafnium dichloride;

bis(N-methyl-5,6-dihydroindeno[2,1-b]indol-6-yl) titanium dichloride;

bis(N-methyl-5,6-dihydroindeno[2,1-b]indol-6-yl) zirconium dichloride;

bis(N-methyl-5,6-dihydroindeno[2,1-b]indol-6-yl) hafnium dichloride;

bis(N-phenyl-5,6-dihydroindeno[2,1-b]indol-6-yl) titanium dichloride;

bis(N-phenyl-5,6-dihydroindeno[2,1-b]indol-6-yl) zirconium dichloride;

bis(N-phenyl-5,6-dihydroindeno[2,1-b]indol-6-yl) hafnium dichloride;

bis(N-methyl-1,8-dihydroindeno [2,1-b]pyrrol-8-yl) zirconium dichloride;

bis(N-methyl-2-methyl-1,8-dihydroindeno[2,1-b]pyrrol-8-yl)zirconium dichloride;
bis(N-phenyl-2-methyl-1,8-dihydroindeno[2,1-b]pyrrol-8-yl)zirconium dichloride;
(N-methyl-5,10-dihydroindeno[1,2-b]indol-10-yl)(fluorenyl) zirconium dichloride;
(N-methyl-5,10-dihydroindeno[1,2-b]indol-10-yl)(octahydrofluorenyl) zirconium dichloride;
(N-methyl-5,10-dihydroindeno[1,2-b]indol-10-yl)(cyclopentadienyl) zirconium dichloride;
(N-methyl-5,10-dihydroindeno[1,2-b]indol-10-yl)(3-$^t$butyl-cyclopentadienyl)zirconium dichloride;
(N-methyl-5,10-dihydroindeno[1,2-b]indol-10-yl)(3-adamantylcyclopentadienyl) zirconium dichloride;
(N-methyl-5,10-dihydroindeno[1,2-b]indol-10-yl)(fluorenyl) zirconium dichloride;
(N-methyl-5,6-dihydroindeno[2,1-b]indol-6-yl)(fluorenyl) zirconium dichloride;
(N-methyl-5,6-dihydroindeno[2,1-b]indol-6-yl)(octahydrofluorenyl)zirconium dichloride;
(N-methyl-5,6-dihydroindeno[2,1-b]indol-6-yl)(cyclopentadienyl) zirconium dichloride;
(N-methyl-1,8-dihydroindeno[2,1-b]pyrrol-8-yl)(cyclopentadienyl) zirconium dichloride;
(N-methyl-5,8-dihydroindeno[2,1-b]pyrrol-8-yl)(fluorenyl) zirconium dichloride;
(N-phenyl-5,6-dihydroindeno[2,1-b]indol-6-yl)(fluorenyl) zirconium dichloride;
(N-phenyl-5,6-dihydroindeno[2,1-b]indol-6-yl)(2,7-di-t-butyl-fluorenyl) zirconium dichloride;
(N-phenyl-5,6-dihydroindeno[2,1-b)indol-6-yl)(octahydrofluorenyl)zirconium dichloride;
(N-phenyl-5,6-dihydroindeno[2,1-b]indol-6-yl)(cyclopentadienyl) zirconium dichloride;
and the corresponding titanium, zirconium or hafnium dimethyl derivatives.

Another advantageous class of metallocenes according to the present invention corresponds to formula (I) wherein n is different from 0, r is equal to 1 and the groups Cp and A, preferably the same, corresponds to cyclopentadienyl heterocyclic derivatives of formula (II) or (II'); preferably, the divalent group $(ZR^1_m)_n$ is $Si(CH_3)_2$, $SiPh_2$, $CH_2$, $(CH_2)_2$ or $C(CH_3)_2$; even more preferably, it is $Si(CH_3)_2$ or $CH_2$.

Non limitative examples of said metallocenes are:
dimethylsilanediyl-bis(N-methyl-5,10-dihydroindeno[1,2-b]indol-10-yl) titanium dichloride;
dimethylsilanediyl-bis(N-methyl-5,10-dihydroindeno[1,2-b]indol-10-yl) zirconium dichloride;
dimethylsilanediyl-bis(N-methyl-5,10-dihydroindeno[1,2-b]indol-10-yl) hafnium dichloride;
ethylen-bis(N-methyl-5,10-dihydroindeno[1,2-b]indol-10-yl) zirconium dichloride;
isopropyliden-bis(N-methyl-5,10-dihydroindeno[1,2-b]indol-10-yl) zirconium dichloride;
dimethylsilanediyl-bis(N-phenyl-5,10-dihydroindeno[1,2-b]indol-10-yl) zirconium dichloride;
ethylen-bis(N-phenyl-5,10-dihydroindeno[1,2-b]indol-10-yl) zirconium dichloride;
isopropyliden-bis(N-phenyl-5,10-dihydroindeno[1,2-b]indol-10-yl) zirconium dichloride;
dimethylsilanediyl-bis(N-methyl-5,6-dihydroindeno[2,1-b]indol-6-yl)titanium dichloride;
dimethylsilanediyl-bis(N-methyl-5,6-dihydroindeno[2,1-b]indol-6-yl)zirconium dichloride;
dimethylsilanediyl-bis(N-methyl-5,6-dihydroindeno[2,1-b]indol-6-yl)hafnium dichloride;
dimethylsilanediyl-bis(N-methyl-1,8-dihydroindeno[2,1-b]pyrrol-8-yl)zirconium dichloride;
methylen-bis(N-methyl-5,6-dihydroindeno[2,1-b]indol-6-yl)zirconium dichloride;
metlylen-bis(N-methyl-1,8-dihydroindeno[2,1-b]pyrrol-8-yl)zirconium dichloride;
ethylen-bis(N-methyl-5,6-dihydroindeno[2,1-b]indol-6-yl)zirconium dichloride;
isopropyliden-bis(N-methyl-5,6-dihydroindeno[2,1-b]indol-6-yl)zirconium dichloride;
isopropyliden-bis(N-methyl-1,8-dihydroindeno[2,1-b]pyrrol-8-yl)zirconium dichloride;
dimethylsilanediyl-bis(N-phenyl-5,6-dihydroindeno[2,1-b]indol-6-yl)zirconium dichloride;
methylen-bis(N-phenyl-5,6-dihydroindeno[2,1-b]indol-6-yl)zirconium dichloride;
ethylen-bis(N-phenyl-5,6-dihydroindeno[2,1-b]indol-6-yl)zirconium dichloride;
isopropyliden-bis(N-phenyl-5,6-dihydroindeno[2,1-b]indol-6-yl)zirconium dichloride;
dimethylsilanediyl-(N-methyl-5,10-dihydroindeno[1,2-b]indol-10-yl)(cyclopentadienyl)zirconium dichloride;
dimethylsilanediyl-(N-phenyl-5,10-dihydroindeno[1,2-b]indol-10-yl)(cyclopentadienyl) zirconium dichloride;
ethylen(N-methyl-5,10-dihydroindeno[1,2-b]indol-10-yl)(cyclopentadienyl)zirconium dichloride;
ethylen(N-phenyl-5,10-dihydroindeno[1,2-b]indol-10-yl)(cyclopentadienyl)zirconium dichloride;
isopropyliden(N-methyl-5,10-dihydroindeno(1,2-b]indol-10-yl)(cyclopentadienyl)zirconium dichloride;
isopropyliden-bis(N-phenyl-5,10-dihydroindeno[1,2-b]indol-10-yl)(cyclopentadienyl) zirconium dichloride;
and the corresponding zirconium dimethyl derivatives.

A particularly preferred metallocene is methylen-bis(N-methyl-5,6-dihydroindeno[2,1-b]indol6-yl)zirconium dichloride or dimethyl.

Another object of the present invention is a class of ligands of formula (IV):

$$(ZR^1_m)_n(CP)(A) \qquad (IV)$$

wherein the variables Cp, A, $(ZR^1_m)_n$, Z, $R^1$ and m have the meanings reported above and n is an integer ranging from 1 to 4. Said ligands are useful as intermediates in the preparation of the metallocenes according to the present invention.

In the above bridged ligands, the divalent bridge $(ZR^1_m)_n$ is preferably selected from the group consisting of $Si(CH_3)_2$, $SiPh_2$, $CH_2$, $(CH_2)_2$ and $C(CH_3)_2$.

Cp is a heterocyclic cyclopentadienyl group of formula (II) or (II'), reported above, and preferably corresponds to formula (III), reported above; even more preferably, Cp is selected from the group consisting of N-methyl-5,10-dihydroindeno[1,2-b]indolyl, N-phenyl-5,10-dihydroindeno[1,2-b]indolyl, N-allyl-5,10-dihydroindeno[1,2-b]indolyl, N-methyl-5,6-dihydroindeno[2,1-b]indolyl, N-phenyl-5,6-dihydroindeno[2,1-b]indolyl, N-allyl-5,6-dihydroindeno[2,1-b]indolyl and N-methyl-1,8-dihydroindeno[2,1-b]pyrrolyl.

The group A can be a cyclopentadienyl derivative or a group of formula (II) or (II'), and preferably of formula (III); even more preferably, A is equal to Cp.

Non limitative examples of the bridged ligands according to the present invention are:

10-[1,1-dimethyl-1-(5,10-dihydroindeno[1,2-b]indol-10-yl)silyl]-5,10-dihydroindeno[1,2-b]indole;
10-[(5,10-dihydroindeno[1,2-b]indol-10-yl)methyl]-5,10-dihydroindeno[1,2-b]indole;
10-[2-(5,10-dihydroindeno[1,2-b]indol-10-yl)ethyl]-5,10-dihydroindeno[1,2-b]indole;
10-[1-methyl-1-(5,10-dihydroindeno[1,2-b]indol-10-yl)ethyl]-5,10-dihydroindeno[1,2-b]indole;
10-[1,1-dimethyl-1-(N-methyl-5,10-dihydroindeno[1,2-b]indol-10-yl)silyl]-N-methyl-5,10-dihydroindeno[1,2-b]indole;
10-[(N-methyl-5,10-dihydroindeno[1,2-b]indol-10-yl)methyl]-N-methyl-5,10-dihydroindeno[1,2-b]indole;
10-[2-(N-methyl-5,10-dihydroindeno[1,2-b]indol-10-yl)ethyl]-N-methyl-5,10-dihydroindeno[1,2-b]indole;
10-[1-methyl-1-(N-methyl-5,10-dihydroindeno[1,2-b]indol-10-yl)ethyl]-N-methyl-5,10-dihydroindeno[1,2-b]indole;
10-[1,1-dimethyl-1-(N-phenyl-5,10-dihydroindeno[1,2-b]indol-10-yl)silyl]-N-phenyl-5,10-dihydroindeno[1,2-b]indole;
10-[(N-phenyl-5,10-dihydroindeno[1,2-b]indol-10-yl)methyl]-N-phenyl-5,10-dihydroindeno[1,2-b]indole;
10-[2-(N-phenyl-5,10-dihydroindeno[1,2-b]indol-10-yl)ethyl]-N-phenyl-5,10-dihydroindeno[1,2-b]indole;
10-[1-methyl-1-(N-phenyl-5,10-dihydroindeno[1,2-b]indol-10-yl)ethyl]-N-phenyl-5,10-dihydroindeno[1,2-b]indole;
6-[1,1-dimethyl-1-(5,6-dihydroindeno[2,1-b]indol-6-yl)silyl]-5,6-dihydroindeno[2,1-b]indole;
6-[(5,6-dihydroindeno[2,1-b]indol-6-yl)methyl]-5,6-dihydroindeno[2,1-b]indole;
6-[2-(5,6-dihydroindeno[2,1-b]indol-6-yl)ethyl]-5,6-dihydroindeno[2,1-b]indole;
6-[1-methyl-1-(5,6-dihydroindeno[2,1-b]indol-6-yl)ethyl]-5,6-dihydroindeno[2,1-b]indole;
6-[1,1-dimethyl-1-(N-methyl-5,6-dihydroindeno[2,1-b]indol-6-yl)silyl]-N-methyl-5,6-dihydroindeno[1,2-b]indole;
8-[1,1-dimethyl-1-(N-methyl-1,8-dihydroindeno[2,1-b]pyrrol-8-yl)silyl]-N-methyl-1,8-dihydroindeno[1,2-b]pyrrole;
6-[(N-methyl-5,6-dihydroindeno[2,1-b]indol-6-yl)methyl]-N-methyl-5,6-dihydroindeno[2,1-b]indole;
8-[(N-methyl-1,8-dihydroindeno[2,1-b]pyrrol-8-yl)methyl]-N-methyl-1,8-dihydroindeno[2,1-b]pyrrole;
6-[2-(N-methyl-5,6-dihydroindeno[2,1-b]indol-6-yl)ethyl]-N-methyl-5,6-dihydroindeno[2,1-b]indole;
6-[1-methyl-1-(N-methyl-5,6-dihydroindeno[2,1-b]indol-6-yl)ethyl]-N-methyl-5,6-dihydroindeno[2,1-]indole;
6-[1,1-dimethyl-1-(N-phenyl-5,6-dihydroindeno[2,1-b]indol-6-yl)silyl]-N-phenyl-5,6-dihydroindeno[2,1-b]indole;
6-[(N-phenyl-5,6-dihydroindeno[2,1-b]indol-6-yl)methyl]-N-phenyl-5,6-dihydroindeno[2,1-b]indole;
6-[2-(N-phenyl-5,6-dihydroindeno[2,1-b]indol-6-yl)ethyl]-N-phenyl-5,6-dihydroindeno[2,1-b]indole;
6-[1-methyl-1-(N-phenyl-5,6-dihydroindeno[2,1-b]indol-6-yl)ethyl]-N-phenyl-5,6-dihydroindeno[2,1-b]indole;
10-[1,1-dimethyl-1-(cyclopentadienyl)silyl]-N-methyl-5,10-dihydroindeno[1,2-b]indole;
10-[(cyclopentadienyl)methyl]-N-methyl-5,10-dihydroindeno[1,2-b]indole;
10-[2-(cyclopentadienyl)ethyl]N-methyl-5,10-dihydroindeno[1,2-b]indole;
10-[2-(cyclopentadienyl)ethyl]N-phenyl-5,10-dihydroindeno[1,2-b]indole;
10-[1-methyl-1-(cyclopentadienyl)ethyl]N-methyl-5,10-dihydroindeno[1,2-b]indole;
10-[1-methyl-1-(3-$^t$butyl-cyclopentadienyl)ethyl]N-methyl-5,10-dihydroindeno[1,2-b]indole;
10-[1-methyl-1-(3-adamantyl-cyclopentadienyl)ethyl]N-methyl-5,10-dihydroindeno[1,2-b]indole;
10-[1,1-methyl-1-(fluorenyl)silyl]-N-methyl-5,10-dihydroindeno[1,2-b]indole;
10-[(fluorenyl)methyl]-N-methyl-5,10-dihydroindeno[1,2-b]indole;
10-[2-(fluorenyl)ethyl]-N-methyl-5,10-dihydroindeno[1,2-b]indole;
10-[1-methyl-1-(fluorenyl)ethyl]N-methyl-5,10-dihydroindeno[1,2-b]indole;
6-[1,1-dimethyl-1-(cyclopentadienyl)silyl]-N-methyl-5,6-dihydroindeno[2,1-b]indole; 6-[(cyclopentadienyl)methyl]-N-methyl-5,6-dihydroindeno[2,1-b]indole;
6-[1,1-dimethyl-1-(fluorenyl)silyl]-N-methyl-5,6-dihydroindeno[2,1-b]indole;
6-[1,1-dimethyl-1-(2,7-di-butyl-fluorenyl)silyl]-N-methyl-5,6-dihydroindeno[2,1-b]indole;
6-[1-methyl-1-(fluorenyl)ethyl]N-methyl-5,6-dihydroindeno[2,1-b]indole.

A particularly preferred bridged ligand is 6-[(N-methyl-5,6-dihydroindeno[2,1-]indol-6-yl)methyl]-N-methyl-5,6-dihydroindeno[2,1-b]indole.

The ligands of the invention can be prepared according to general procedures known in the state of the art, starting from commercially obtainable products or from derivatives which can be prepared by known methods. More specifically, when the group A is equal to the group Cp, the above ligands can be prepared by first reacting a compound of formula (V) or (V'):

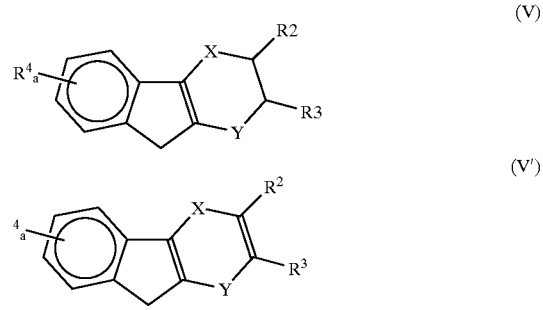

wherein X, Y, $R^2$, $R^3$, $R^4$ and a have the meanings reported above, with a compound able to form a delocalized anion on the cyclopentadienyl ring, and thereafter with a compound of formula $(ZR^1{}_m)_nW_2$, wherein Z, $R^1$, m and n are defined as above and the substituents W, same or different from each other, are halogen atoms or tosylate groups. Non limitative examples of compounds of formula $(ZR^1{}_m)_nW_2$ are dimethyldichlorosilane, diphenyldichlorosilane, dimethyldichlorogermanium, 2,2-dichloropropane and 1,2-dibromo-ethane.

The synthesis of the above bridged ligands is preferably carried out by adding a solution of an organic lithium compound in an apolar solvent to a solution of the compound (V) or (V') in an aprotic polar solvent. The thus obtained solution containing the compound (V) or (V') in the anionic form is then added to a solution of the compound of formula $(ZR_m)_nW_2$ in an aprotic polar solvent. The bridged ligand can be finally separated by general procedures known in the state of the art.

Not limitative examples of aprotic polar solvents which can be used in the above process are tetrahydrofurane, dimethoxyethane, diethylether, toluene and dichloromethane. Not limitative examples of apolar solvents suitable for the above process are pentane, hexane and benzene.

During the whole process, the temperature is preferably kept between −180° C. and 80° C., and more preferably between −20° C. and 40° C.

The preparation of the bridged ligands of formula (IV), when the group A is different from the group Cp, can be carried out by reacting an anionic salt of a compound of formula A) or (V') with a substituted A group.

The metallocene compounds of formula (I), when n is different from 0 and r is 1, can be prepared by first reacting the bridged ligands $(ZR^1_m)_n(Cp)(A)$, prepared as described above, with a compound able to form a delocalized anion on the cyclopentadienyl rings, and thereafter with a compound of formula $ML_4$, wherein M and the substituents L are defined as above. Non limitative examples of compounds of formula $ML_4$ are titanium tetrachloride, zirconium tetrachloride and hafnium tetrachloride.

More specifically, said bridged ligands are dissolved in an aprotic polar solvent and to the obtained solution is added a solution of an organic lithium compound in an apolar solvent. The thus obtained anionic form is separated, dissolved in an aprotic polar solvent and thereafter added to a suspension of the compound $ML_4$ in an aprotic polar solvent. At the end of the reaction, the solid product obtained is separated from the reaction mixture by techniques commonly used in the state of the art. Not limitative examples of aprotic polar solvents suitable for the above reported processes are tetrahydrofurane, dimethoxyethane, diethylether, toluene and dichloromethane. Not limitative examples of apolar solvents suitable for the above process are pentane, hexane and benzene.

During the whole process, the temperature is preferably kept between −180° C. and 80° C., and more preferably between −20° C. and 40° C.

The metallocene compounds of formula (I), wherein n=0 and r=1, can be prepared by reacting the anions of the ligands Cp and A with a tetrahalide of the metal M (i.e. $ML_4$), M and L having the meanings reported above, said reaction being carried out in a suitable solvent.

Metallocene compounds of formula (I) according to the present invention, wherein Cp and A are partially hydrogenated, can be suitably prepared by hydrogenation of the corresponding metallocene compounds in which Cp and optionally A corresponds to formula (I) or (II'). The hydrogenation reaction is carried out in a suitable solvent such as $CH_2Cl_2$, in the presence of a suitable hydrogenation catalyst such as $PtO_2$, and hydrogen. Hydrogen pressure is preferably comprised between 1 and 100 bar, and the temperature is preferably comprised between −50 and 50° C.

When at least one L substituent in the metallocene compound of formula (I) is different from halogen, it is necessary to substitute at least one substituent L in the obtained metallocene with at least another substituent different from halogen. Such a substitution reaction is carried out by methods known in the state of the art. For example, when the substituents L are alkyl groups, the metallocenes can be reacted with alkylmagnesium halides (Grignard reagents) or with lithiumalkyl compounds.

A further object of the present invention is a catalyst for the polymerization of olefins comprising the reaction product between:
(1) a metallocene compound of formula (I), optionally as a reaction product with an organo-aluminum compound of formula $AlR^7_3$ or $Al_2R^7_6$, in which the substituents $R^7$, same or different from each other, have the meaning of $R^4$ or are halogen, and;
(2) an alumoxane, optionally in admixture with an organo-aluminum compound of formula $AlR_3$ or $Al_2R^7$, the substituents $R^7$ having the meanings reported above, or one or more compounds capable of forming an alkyl metallocene cation.

The alumoxane used as component (2) can be obtained by reacting water with the organo-aluminum compound of formula $AlR^7_3$ or $Al_2R^7_6$, with the condition that at least one $R^7$ is not halogen. In this case, the molar ratios of Al/water in the reaction is comprised between 1:1 and 100:1.

The molar ratio between aluminum and the metal of the metallocene is comprised between about 10:1 and about 5000:1, and preferably between about 100:1 and about 4000:1.

The alumoxane used in the catalyst according to the invention is believed to be a linear, branched or cyclic compound, containing at least one group of the type:

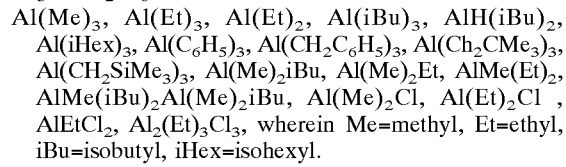

wherein the substituents $R^8$, same or different from each other, have the meaning of $R^4$ or are a group $—O—Al(R^8)_2$.

Examples of alumoxanes suitable for the use according to the present invention are methylalumoxane (MAO), isobutylalumoxane (TIBAO) and tris(2,4,4-trimethyl-pentyl) aluminoxane (TOAO).

Mixtures of different alumoxanes are suitable as well. Not limitative examples of aluminum compounds of formula $AlR^7_3$ or $Al_2R^7_6$ are:

$Al(Me)_3$, $Al(Et)_3$, $Al(Et)_2$, $Al(iBu)_3$, $AlH(iBu)_2$, $Al(iHex)_3$, $Al(C_6H_5)_3$, $Al(CH_2C_6H_5)_3$, $Al(Ch_2CMe_3)_3$, $Al(CH_2SiMe_3)_3$, $Al(Me)_2iBu$, $Al(Me)_2Et$, $AlMe(Et)_2$, $AlMe(iBu)_2Al(Me)_2iBu$, $Al(Me)_2Cl$, $Al(Et)_2Cl$ , $AlEtCl_2$, $Al_2(Et)_3Cl_3$, wherein Me=methyl, Et=ethyl, iBu=isobutyl, iHex=isohexyl.

Among the above mentioned aluminum compounds, tris-(2,4,4-trimethyl-pentyl)aluminum (TIOA), trimethylaluminum (TMA) and triisobutylaluminum (TIBA) are preferred.

Not limitative examples of compounds able to form a metallocene alkyl cation are compounds of formula $J^+K^-$, wherein $J^+$ is a Bronsted acid, able to give a proton and to react irreversibly with a substituent of the compound of formula (I) and $K^-$ is a compatible anion, which does not coordinate, which is able to stabilize the active catalytic species which originates from the reaction of the two compounds and which is sufficiently labile to be able to be removed from an olefinic substrate. Preferably, the anion $K^-$ comprises one or more boron atoms. More preferably, the anion $K^-$ is an anion of the formula $BAr^{(-)}_4$, wherein substituents Ar, same or different from each other, are aryl radicals such as phenyl, pentafluorophenyl, bis-(trifluoromethyl)-phenyl. Particularly preferred is the tetrakis-pentafluorophenyl-borate. Furthermore, compounds of formula $BAr_3$ can be suitably used.

The catalysts of the present invention can also be used on an inert support, by depositing the metallocene component (1), or the reaction product of the metallocene component (1) with component (2), or the component (2) and successively the metallocene component (1), on the inert support, such as silica, alumina, styrene-divinylbenzene copolymers or polyethylene.

The solid compound so obtained, in combination with further addition of the alkyl aluminum compound as such or prereacted with water, is usefully employed in gas phase polymerization.

The catalysts of the present invention can be advantageously used in homo or copolymerization of olefins. Therefore, a further object of the invention is a process for the polymerization of olefins, comprising the polymerization reaction of at least one olefinic monomer in the presence of the above described catalyst.

When is used a metallocene compound of formula (I), wherein n=1 and the group A is a non-substituted cyclopentadienyl group, the obtained α-olefin homopolymers have a predominantly syndiotactic structure. Alternatively, when is used a metallocene of formula (1), wherein n=1 and the group A is a substituted cyclopentadienyl group, the obtained α-olefin homopolymers have an isotactic structure.

The catalysts of the present invention can be used in the homo-polymerization reaction of olefins, preferably of ethylene for the preparation of HDPE, or of α-olefins, such as propylene and 1-butene. In ethylene polymerization, the metallocenes of the invention show excellent activities even when used in very low Zr/Al ratios.

Another interesting use of the catalysts according to the present invention is in the copolymerization of ethylene with higher olefins. In particular, the catalysts of the invention can be used for the preparation of LLDPE. The LLDPE copolymers which are obtained have a density higher than 0.9 g/ml and very low xylene soluble percentages.

Suitable olefins to be used as comonomers comprise α-olefins of the formula $CH_2=CHR$, wherein R is an alkyl radical having from 1 to 10 carbon atoms, and cycloolefis. Examples of these olefins are propylene, 1-butene, 1-pentene, 4-methyl-1-pentene, 1-hexene, 1-octene, 1-decene, 1-dodecene, 1-tetradecene, 1-esadecene, 1-octadecene, 1-eicosene, allylcyclohexane, cyclopentene, cyclohexene, norbornene and 4,6-dimethyl-1-heptene.

The copolymers may also contain small proportions of units deriving from polyenes, in particular from straight or cyclic, conjugated or non conjugated dienes, such as 1,4-hexadiene, isoprene, 1,3-butadiene, 1,5-hexadiene and 1,6-heptadiene. The units deriving from α-olefins of formula $CH_2=CHR$, from cycloolefins and/or from polyenes are present in the copolymers preferably in amounts ranging from 1 % to 20% by mole.

The catalyst of the invention can also be used for the preparation of elastomeric copolymers of ethylene with α-olefins of formula $CH_2=CHR$, R having the meaning reported above, optionally containing small quantities of units deriving from polyenes.

The saturated elastomeric copolymers can contain ethylene units and α-olefins and/or non conjugated diolefins able to cylopolymerize. The unsaturated elastomeric copolymers can contain, together with the units deriving from the polymerization of ethylene and α-olefins, also small proportions of unsaturated units deriving from the copolymerization of one or more polyenes. The content of unsaturated units is preferably comprised between 0.1 and 5% by weight.

Non limitative examples of suitable α-olefins comprise propylene, 1-butene and 4-methyl-1-pentene. Suitable non conjugated diolefins able to cyclopolymerize comprise 1,5-hexadiene, 1,6-heptadiene and 2-methyl-1,5-hexadiene.

Non Limitative Examples of Suitable Polyenes are:
(i) polyenes able to give unsaturated units, such as:
linear, non-conjugated dienes, such as 1,4-hexadiene trans, 1,4-hexadiene cis, 6-methyl-1,5-heptadiene, 3,7-dimethyl-1,6-octadiene and 11-methyl-1,10-dodecadiene;
monocyclic diolefins, such as cis-1,5-cyclooctadiene and 5-methyl-1,5-cyclooctadiene;
bicyclic diolefins, such as 4,5,8,9-tetrahydroindene and 6 and 7-methyl-4,5,8,9-tetrahydroindene;
alkenyl or alklyliden norbornenes, such as 5-ethlyliden-2-norbornene, 5-isopropyliden-2-norbornene and exo-5-isopropenyl-2-norbornene;
polycyclic diolefins, such as dicyclopentadiene, tricyclo-[6.2.1.0$^{2.7}$]4,9-undecadiene and the 4-methyl derivative thereof;
(ii) non-conjugated diolefins able to cyclopolymerize, such as 1.5-hexadiene, 1,6-heptadiene and 2-methyl-1,5-hexadiene;
(iii) conjugated dienes, such as butadiene and isoprene.

Another object of the present invention is a process for the polymerization of propylene carried out in the presence of the above described catalyst.

A further interesting use of the catalysts according to the present invention is for the preparation of cycloolefin polymers. Monocyclic and polycyclic olefin monomers can be either homopolymerized or copolymerized, also with linear olefin monomers.

Polymerization processes according to the present invention can be carried out in gaseous phase or in liquid phase, optionally in the presence of an inert hydrocarbon solvent either aromatic (such as toluene), or aliphatic (such as propane, hexane, heptane, isobutane and cyclohexane).

The polymerization temperature is preferably ranging from about 0° C. to about 250° C. In particular, in the processes for the preparation of HDPE and LLDPE, it is preferably comprised between 20° C. and 150° C. and, more preferably between 40° C. and 90° C., whereas for the preparation of the elastomeric copolymers it is preferably comprised between 0° C. and 200° C. and, more preferably between 20° C. and 100° C.

The molecular weight of the polymers can be varied by changing the polymerization temperature, the type or the concentration of the catalyst components or by using molecular weight regulators, such as hydrogen. The fact that the catalysts of the invention are sensitive to hydrogen as a molecular weight regulator is unexpected in view of the fact that, if the polymerization is carried out in the presence of a metallocene compound according to the cited EP 0 604 908, the hydrogen has no effect on the molecular weight of the obtained polymers, even if used in relevant amounts.

The molecular weight distribution can be varied by using mixtures of different metallocenes or by carrying out the polymerization in various steps differing in the polymerization temperature and/or in the concentration of the molecular weight regulators.

The polymerization yield depends on the purity of metallocenes in the catalyst; the metallocene according to the present invention may be used as such or may be previously subjected to purification treatments.

Particularly interesting results are obtained when the components of the catalyst are contacted among them before the polymerization. The contact time is generally comprised between 1 and 60 minutes, preferably between 5 and 20 minutes. The pre-contact concentrations for the metallocene component (1) are comprised between $10^{-2}$ and $10^{-8}$ mol/l, whereas for the component (2) they are comprised between 10 and $10^{-3}$ mol/l. The precontact is generally carried out in the presence of a hydrocarbon solvent and, optionally, of small amounts of monomer.

The following examples are reported for illustrative and not limitative purposes.

GENERAL PROCEDURES AND CHARACTERIZATIONS

All operations were performed under nitrogen by using conventional Schlenk-line techniques. Solvents were distilled from blue Na-benzophenone ketyl ($Et_2O$), $CaH_2$ ($CH_2Cl_2$) or $AliBu_3$ (hydrocarbons), and stored under nitrogen. BuLi (Aldrich) was used as received. The $^1$H-NMR analyses of metallocenes and ligands were carried out on an AC200 Bruker spectrometer ($CD_2Cl_2$, referenced against the middle peak of the triplet of the residual $CHDCl_2$ at 5.35 ppm). All NMR solvents were dried over $P_2O_5$ and distilled before use. Preparation of the samples was carried out under nitrogen using standard inert atmosphere techniques.

The $^1$H-NMR and 13C-NMR analyses of polymers were carried out on a Bruker 400 MHz instrument. The samples were analyzed as solutions in tetrachlorodideuteroethane at 130° C. The intrinsic viscosity [η] (dl/g) was measured in tetralin at 135° C.

The melting point Tm (° C.) and ΔH (J/g) of the polymers were measured by Differential Scanning Calorimetry (DSC) on a DSC-7 apparatus of Perkin Elmer Co. Ltd., according to the following procedure: about 10 mg of sample obtained from the polymerization were heated to 180° C. with a scanning speed equal to 20° C./minute; the sample was kept at 180° C. for 5 minutes and thereafter was cooled with a scanning speed equal to 20° C./minute. A second scanning was then carried out according to the same modalities as the first one. The reported values are the ones obtained in the second scanning.

The density (g/ml) was determined by immersion of a sample of extruded copolymer in a column with a density gradient according to the ASTM D-1505 method.

In the copolymers according to the present invention, the product of the reactivity ratios $r_1r_2$, wherein $r_1$ is the reactivity ratio of propylene and $r_2$ that of ethylene, was calculated according to the following formula:

$$r_1 \times r_2 = 1 + f \times (c+1) - (f+1) \times (c+1)^{1/2}$$

wherein f is the ratio between moles of ethylene units and moles of propylenic units in the copolymer, and c is (PPP+PPE)/EPE.

The amount of comonomers (% wt.) in the copolymer was determined by IR techniques. The solubility in xylene at 25° C. was determined according to the following modalities: about 2.5 g of polymer and 250 ml of xylene were placed in a round-bottomed flask provided with cooler and reflux condenser, kept under nitrogen. The thus obtained mixture was heated to 135° C. and was kept under stirring for about 60 minutes. The mixture was allowed to cool to 25° C., under continuous stirring; then, it was filtered off and after evaporation of the solvent from the filtrate until the obtainment of a constant weight, the weight of the soluble portion was calculated.

PREPARATION OF COMPOUNDS OF FORMULA (V) or (V')

Example 1

Synthesis of 5,10-Dihydroindeno[1,2-b]indole of Formula (V), Wherein X=N=H, Y is a Single Bond, $R^2$ and $R^3$ Form a Condensed Benzene Ring and a=0

The N—H indenoindole was prepared as described by H. Armit and R. Robinson (*J. Chem. Soc.*, 121:835), according to the following reaction scheme:

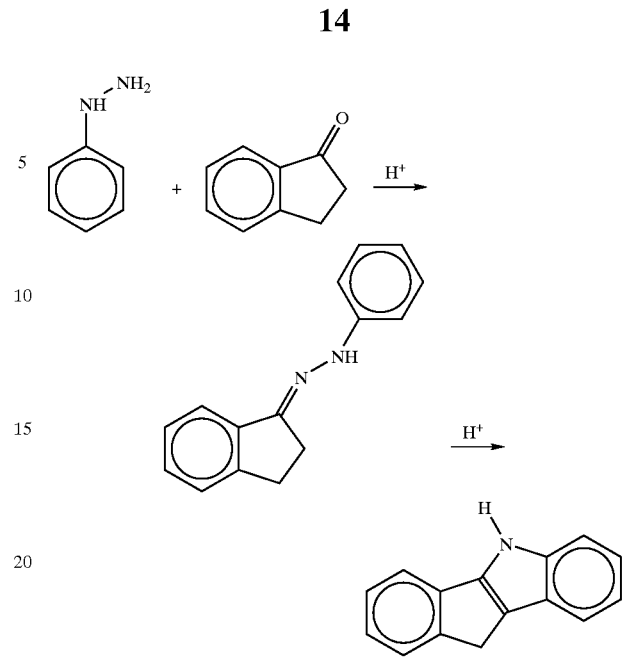

Example 2

Synthesis of N-Methyl-5,10-dihydroindeno[1,2-b] indole of Formula (V), Wherein X=N—Me, Y is a Single Bond, $R^2$ and $R^3$ Form a Condensed Benzene Ring and a=0

In a 0.5 l bulb were placed 100 ml 50% aqueous NaOH, 100 ml benzene, 6.1 g (28 mmol) of 5,10-dihydroindeno[1,2-b]indole, prepared in the Example 1,1.8 ml (28 mmol) of MeI and o.5 g of trimethylcetylammonium bromide. After having stirred the obtained mixture for 2 hours, the formation of an organic phase was observed; said phase was separated, washed twice with water (100 ml) and dried over $Na_2SO_4$. After removal of the solvent, the residue was recrystallized from ethanol, obtaining 5.3 g of N-methyl-5,10-dihydroindeno[1,2-b]indole(yield=84%).

$^1$H-NMR (CDCl$_3$): 7.65–7.10 (m, 8H), 4.03 (s, 3H), 3.68 (s, 2H).

Example 3

Synthesis of N-Phenyl-5,10-dihydroindeno[1,2-b] indole of Formula (V), Wherein X=N—Ph, Y is a Single Bond, $R^2$ and $R^3$ Form a Condensed Benzene Ring and a=0

N—Ph indenoindole was synthesized according to the following reaction scheme:

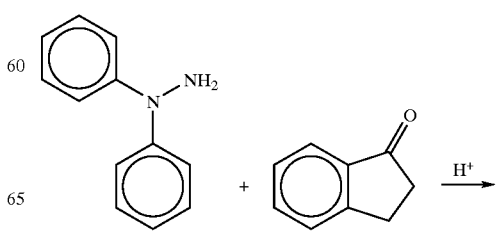

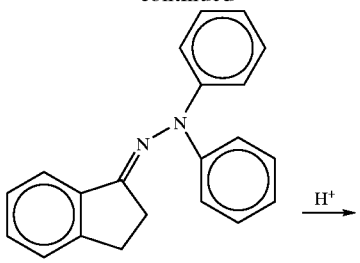

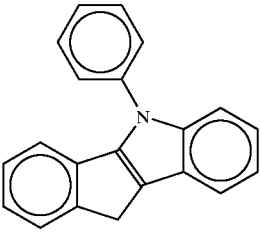

In a 0.25 l bulb were placed 13 g (70 mmol) of N,N-diphenylhydrazine, 9.2 g (70 mmol) of 1-indanone and the solution obtained by mixing 5 ml 96% H2SO4 in 80 ml ethanol. The thus obtained mixture was heated at reflux for 4 hours and it was then poured into a solution of 7.5 g NaOH in 200 ml water.

The thus obtained hydrazide was extracted with $CH_2Cl_2$ (150 ml); the organic phase was separated, dried over $Na_2SO_4$ and the solvent was evaporated. The solid residue was recrystallized from heptane, obtaining 11.3 g of N-phenyl-5,10dihydroindeno[1,2-b]indole (yield=60%).

$^1$H-NMR (CDCl$_3$): 7.75–7.05 (m, 13H), 3.82 (s, 2H).

Example 4

Synthesis of 5,6-dihydroindeno[2,1-b]indole of Formula (V), Wherein X is a Single Bond, Y=N—H, $R^2$ and $R^3$ Form a Condensed Benzene Ring and a=0

The N—H indenoindole was prepared as described by H. Armit and R. Robinson (*J. Chem. Soc.*, 121:838), according to the following reaction scheme:

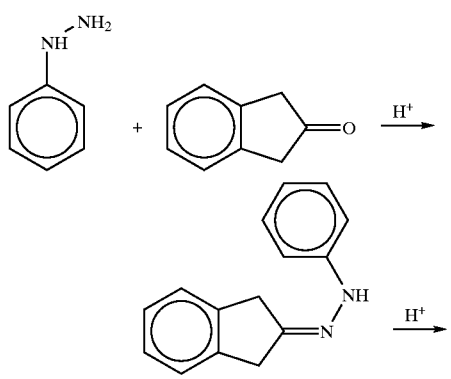

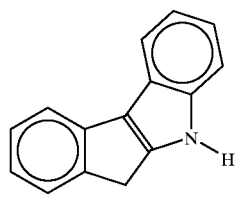

Example 5

Synthesis of N-Methyl-5,6-dihydroindeno[2,1-b]indole of Formula (V), Wherein X is a Single Bond, Y=N—Me, $R^2$ and $R^3$ Form a Condensed Benzene Ring and a=0

In a 0.5 l bulb were placed 100 ml 50% aqueous NaOH, 100 ml benzene, 6.1 g (28 mmol) of 5,6-dihydroindeno[2,1-b]indole, prepared in Example 4, 1.8 ml (28 mmol) of MeI and 0.5 g of trimethylcetylammonium bromide. After having stirred the obtained mixture for 2 hours, the formation of an organic phase was observed; said phase was separated, washed twice with water (100 ml) and dried over $Na_2SO_4$. After removal of the solvent, the residue was recrystallized from ethanol, obtaining 4.8 g of N-methyl-5,6-dihydroindeno[2,1-b]indole (yield=78%).

$^1$H-NMR (CDCl$_3$): 7.85–7.00 (m, 8H); 3.72 (s, 3H); 3.61 (s, 2H).

Example 6

Synthesis of N-Allyl-5,6-dihydroindeno[2,1-b]indole of Formula (V), Wherein X is a Single Bond, Y=N-allyl, $R^2$ and $R^3$ Form a Condensed Benzene Ring and a=0

In a 0.5 l bulb were placed 100 ml 50% aqueous NaOH, 100 ml benzene, 6.1 g (28 mmol) of 5,6-dihydroindeno[2,1-b]indole, prepared in Example 4, 5 g (41 mmol) of allyl-bromide and 0.5 g of trimethylcetylammonium bromide. After having stirred the obtained mixture for 12 hours, the formation of an organic phase was observed; said phase was separated, washed twice with water (100 ml) and dried over $Na_2SO_4$. After removal of the solvent, the residue was passed through a column of silicagel, eluted with hexane/ethylacetate=5:1); the resulting solution was evaporated, obtaining 1.8 g of N-allyl-5,6-dihydroindeno[2,1-b]indole (yield=37%).

$^1$H-NMR (CDCl$_3$): 7.85–6.90 (m, 8H); 5.95 (m, 1H); 5.16 (m, 1H); 5.02 (m, 1H); 4.73 (m,2H); 3.63 (s,2H).

Example 7

Synthesis of N-Phenyl-5,6-dihydroindeno[2,1-b]indole of Formula (V), Wherein X is a Single Bond, Y=N—Ph, $R^2$ and $R^3$ Form a Condensed Benzene Ring and a=0

In a 0.25 l bulb were placed 10 g (45 mmol) of N,N-diphenylhydrazinium chloride, 6.0 g (45 mmol) of 2-indanone and 50 ml of ethanol. The thus obtained mixture was heated at reflux for 4 hours and it was poured into water; the residual mixture was extracted with $CH_2Cl_2$ (150 ml) and the solvent was evaporated. The wanted compound was isolated by passing the obtained mixture through a column of silicagel, eluting with benzene/hexane=1:2. The resulting solution was evaporated and treated with 10 ml of hexane, obtaining the precipitation of crystals. Said crystals were separated, washed with hexane (10 ml) and finally dried, thus yielding 5.4 g of N-phenyl-5,6-dihydroindeno[2,1-b] indole (yield=45%).

$^1$H-NMR (CDCl$_3$): 7.95–7.15 (m, 13H); 3.81 (s, 2H).

Example 8

Synthesis of 2-t-Butyl-5,6-dihydroindeno[2,1-b] indole of Formula (V), Wherein X is a Single Bond, Y=N—H, R$^2$ and R$^3$ Form a Condensed Benzene Ring, a=1 and R$^4$=t-butyl

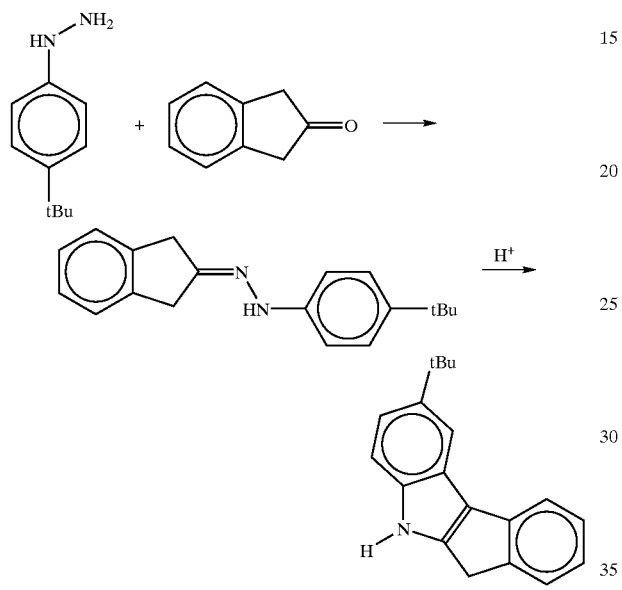

16 g (0.1 mol) of t-butyl-phenylhydrazine, 13 g (0.1 mol) of indan-2-one and 100 ml of isopropanole were placed into a bulb. The obtained mixture was refluxed for 1 hour; then it was treated dropwise with a solution of 5 ml H$_2$SO$_4$ in 30 ml of isopropanole and refluxed for 1 hour. The resulting mixture was cooled to room temperature and poured into water. The precipitate was filtered, washed with water and finally dried, thus yield 18 g of 2-t-butyl-5,6-dihydroindeno[2,1-b]indole (yield=69%).

$^1$H NMR (CDCl$_3$): 8.04(bs, 1H); 7.88(s, 1H); 7.71(d, 1H); 7.42(d, 1H); 7.38(t, 1H); 7.32(dd, 1H); 7.28(d, 1H); 7.12(t, 1H); 3.65(s, 2H); 1.43(s, 9H).

Example 8-bis

Synthesis of 2-Methyl-5,6-dihydroindeno[2,1-b] indole of Formula (V), Wherein X is a Single Bond, Y=N—H, R$^2$ and R$^3$ Form a Condensed Benzene Ring, a=1 and R$^4$=Methyl

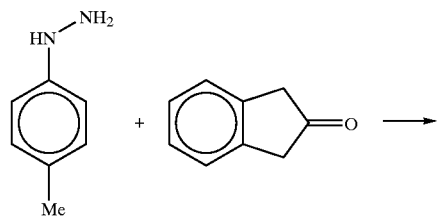

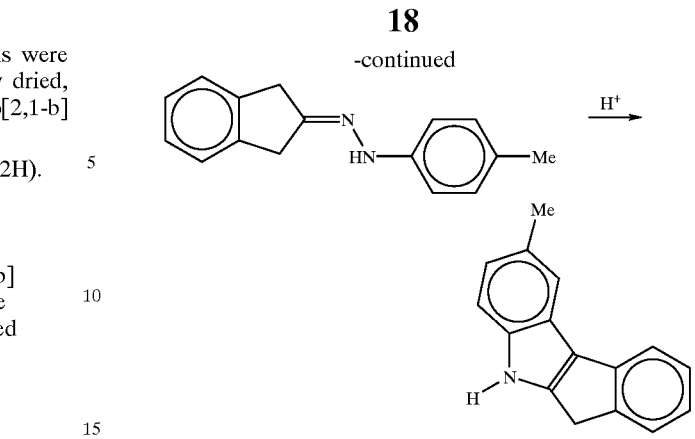

12.2 g (0.01 mol) of p-Me-phenylhydrazine, 13 g (0.1 mol) of indan-2one and 100 ml of isopropanole were placed into a bulb. The obtained mixture was refluxed for 1 hour; the mixture was then treated dropwise with a solution GA 5 ml H$_2$SO$_4$ in 30 ml of isopropanol and refluxed for 1 hour. The resulting mixture was cooled to room temperature and poured into water. The precipitate was filtered, washed with water and finally dried, thus obtaining 19.3 g of 2-methyl-5,6-dihydroindeno[2,1-b]indole (yield=88%).

$^1$H-NMR (CDCl$_3$): 8.03(bs, 1H); 7.65(s, 1H); 7.63(d, 1H); 7.39(d, 1H); 7.33(t, 1H); 7.22(d, 1H); 7.08(t, 1H); 7.01(d, 1H); 3.70(s, 2H); 2.55(s, 3H).

Example 9

Synthesis of N-Methyl-2-t-butyl-5,6-dihydroindeno [2,1-b]indole of Formula (V), Wherein X is a Single Bond, Y=N—Me, R$^2$ and R$^3$ Form a Condensed Benzene Ring, a=1 and R$^4$=t-butyl

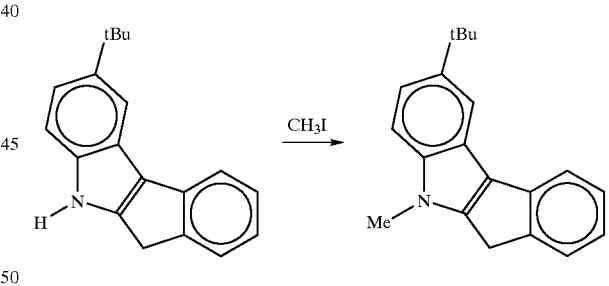

15 g of NaOH, 20 ml of water, 20 ml of benzene, 0.1 g of trimethyl-cetyl-anmmonium bromide, 7.8 g (0.03mol) of 2-t-butyl-5,6-dihydroindeno[2,1-b]indole, obtained in Example 8, and 2.5 ml (0.04mol) of CH$_3$I were placed in a bulb. The resulting two-phase system was stirred for 2 hours at room temperature and then 10 minutes at reflux. The reaction mixture was then cooled to room temperature; the organic layer was collected, washed twice with 100 ml of water and evaporated. The residue was recrystallized from hexane/benzene, thus obtaining 6.2 g of N-methyl-2-t-butyl-5,6-dihydroindeno[2,1-b]indole (yield=75%).

$^1$H NMR (CDCl$_3$): 7.82(d, 1H); 7.64(d, 1H); 7.39(d, 1H); 7.32(t, 1H); 7.30(dd, 1H); 7.24(d, 1H); 7.05(t, 1H); 3.72(s, 3H); 3.62(s, 2H); 1.43(s, 9H)

Example 9-bis

Synthesis of N-Methyl-2-methyl-5,6-dihydroindeno[2,1-b]indole of Formula (V), Wherein X is a Single Bond, Y=N—Me, $R^2$ and $R^3$ Form a Condensed Benzene Ring, a=1 and $R^4$=Methyl

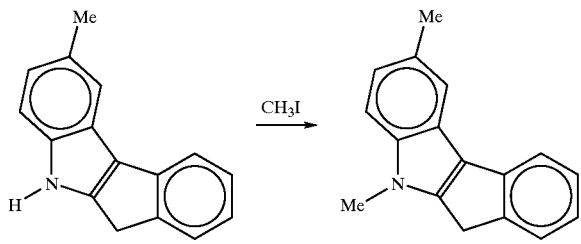

45 g of NaOH, 60 ml of water, 60 ml of benzene, 0.3 g of trimethyl-cethyl-ammonium bromide, 19.3(0.088 mol) of 2-methyl-5,6-dihydroindeno[2,1-b]indole, prepared in Example 8-bis, and 7.5 ml (0.12 mol) of CH$_3$I were placed in a bulb. The resulting two-phase system was stirred for 2 hours at room temperature and then 10 minutes at reflux. Then the reaction mixture cooled to room temperature and filtered. The obtained precipitate was washed twice with ethanol and finally dried, thus obtaining 18 g of N-methyl-2-methyl-5,6-dihydroindeno[2,1-b]indole (yield=88%).

$^1$H-NMR (CDCl$_3$): 7.63(s, 1H); 7.61(d, 1H); 7.38(d, 1H); 7.32(t, 1H); 7.18(d, 1H); 7.05(t, 1H); 7.03(d, 1H); 3.76(s, 3H); 3.62(s, 2H); 2.56(s, 3H).

Example 10

Synthesis of N-Methyl-2-methyl-1,8-dihydroindeno[2,1-b]pyrrole of Formula (V'), Wherein X is a Single Bond, Y=N—Me, $R^2$=H, $R^3$=Me and a=0

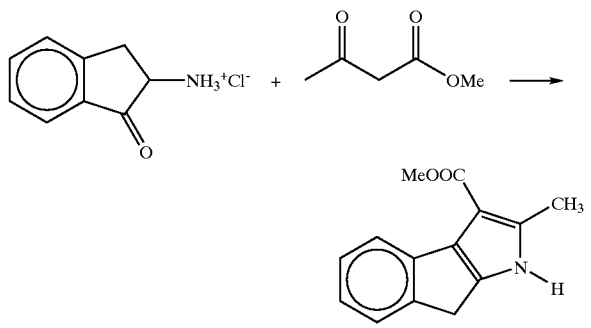

9.2 g (50 mmol) aminoindanone-hydrochloride (prepared as reported by S. Gabriel et al., Chem. Ber. 29:2604–2606, 1986), 23 ml (200 mmol) methylacetoacetic ester and 13.6 g (100 mmol) NaOAc trihydrate were added to 100 ml of acetic acid. The resulting mixture was heated at 80° C. under stirring, for 3 hours. The reaction mixture was then cooled to room temperature; the precipitate was filtered, washed twice with 100 ml of water, ethanol and ether, and was finally dried, thus obtaining 6.6 g of carbomethoxy-indenopyrrole (yield=58%).

$^1$H-NMR(CDCl$_3$): 8.40(bs, 1H); 7.97(d, 1H); 7.37(d, 1H); 7.30(t, 1H); 7.10(td, 1H); 3.95(s, 3H); 3.53(s, 2H); 2.62(s, 3H).

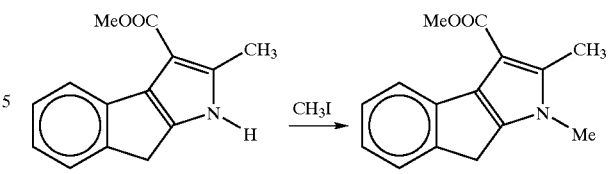

6.5 g (29 mmol) of carbomethoxy-indenopyrrole, prepared as reported above, 3.6 ml (60 mmol) of methyl iodide, 30 ml water, 30 ml of benzene, 10 g NaOH and 100 mg of trimethylcethylammonium chloride were placed into a bulb and the mixture was heated at 40° C., under vigorous stirring, for 3 hours. Then the mixture was cooled to room temperature; the organic phase was separated, the solvent was evaporated and the residue was recrystallized from hexanelbenzene mixture, thus obtaining 4.5 g of N-methylcarbomethoxyindenopyrrole (yield=64%).

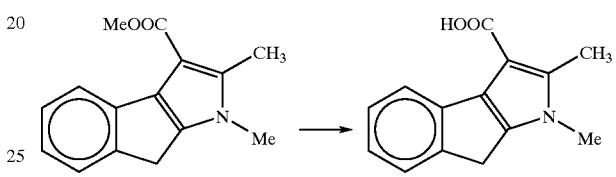

5.54 g (20 mmol) of N-methyl-carbomethoxyindenopyrrole, prepared as reported above, 25 ml of methanol and 25 ml 37 %KOH were placed into a bulb and the resulting mixture was refluxed until the solid dissolves. The resulting solution was cooled to room temperature, washed twice with 50 ml of benzene and neutralized with hydrochloric acid. The precipitate was filtered, washed with water and dried, thus obtaining 3.6 g of N-methyl-indenopyrrolecarbonic acid (yield=85%).

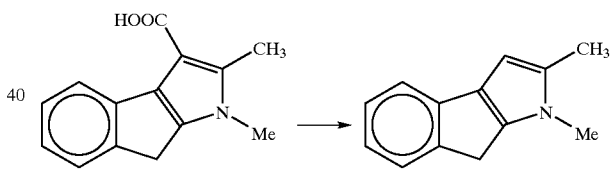

3.6 g (17 mmol) of the obtained compound and 40 ml of diglyme were placed into a bulb. The resulting suspension was heated to 160° C. and kept at this temperature for 2 hours. The reaction mixture was then cooled to room temperature; the crystalline precipitate was filtered, washed with ethanol and finally dried, thus obtaining 2.27 g of N-methyl-2-methyl-1,8-dihydroindeno[2,1-b]pyrrole (yield=79%).

$^1$H-NMR(CDCl$_3$): 7.34(m, 2H); 7.20(t, 1H); 6.98(t, 1H); 6.07(s, 1H); 3.52(s, 3H); 3.48(s, 2H); 2.28(s, 3H).

PREPARATION OF BRIDGED LIGANDS OF FORMULA (IV)

Example 11

Synthesis of 10-[1-Methyl-1-(cyclopentadienyl)ethyl]N-methyl-5,10-dihydroindeno[1,2-b]indole of Formula (IV), Wherein Cp is Like in Ex. 2, A is Cyclopentadienyl and the Bridging Divalent Radical is C(CH$_3$)$_2$ In a 50 ml bulb were placed 1.55 g (7 mmol) of N-methyl-5,10-dihydroindeno[1,2-b]indole, prepared in Example 2, and 10 ml THF. The mixture was cooled to −50° C. and treated with 4.5 ml of BuLi 1.6N (7 mmol) in hexane. The resulting solution was allowed to warm to room temperature and subsequently treated with a solution consisting of 0.75 ml (7 mmol) of 6,6-dimethylfulvene in 5 ml of THF. The thus obtained mixture was stirred under reflux for 2 hours; the resulting suspension was cooled to room temperature and treated with 20 ml water. The mixture was extracted with $CH_2Cl_2$ (50 ml) and the organic phase was dried over $Na_2SO_4$; after evaporation of the solvent, the solid residue was recrystallized from hexane to yield 1.8 g (yield=80%) of a mixture of the two isomers (position of the double bonds) of the ligand 10-[1-methyl-1-(cyclopentadienyl) ethyl]N-methyl-5,10-dihydroindeno[1,2-b]indole.

$^1$H-NMR ($CDCl_3$): 7.6–7.0 (m, 8H); 6.87 (m), 6.64 (m), 6.55 (m), 6.46 (m), 6.22 (m), 5.96 (m) total 3H; 4.13 (s), 4.10 (s) total 1H; 4.03 (s, 3H); 3.22 (m), 3.08 (m) total 2H; 1.47 (s), 1.42 (s), 0.90 (s), 0.89 (s) total 6H.

Example 12

Synthesis of 10-[1-Methyl-1-(3-$^t$butyl-cyclopentadienyl) ethyl]N-methyl-5,10-dihydroindeno[1,2-b]indole Formula (IV), Wherein Cp is Like in Ex. 2, A is 2-$^t$But-cyclopentadienyl and the Bridging Divalent Radical is $C(CH_3)_2$ In a 100 ml bulb were placed 3.07 g (14 mmol) of N-methyl-5,10-dihydroindeno[1,2-b]indole prepared in Example 2 and 20 ml THF. The mixture was cooled to −50° C. and subsequently treated with 9 ml of BuLi 1.6N (14 mmol) in hexane. The resulting solution was allowed to warm to room temperature and subsequently treated with a solution consisting of 2.27 g (14 mmol) of 6,6-dimethyl-2-$^t$butyl-fulvene in 10 ml of THF. The thus obtained mixture was stirred under reflux for 2 hours; the resulting suspension was cooled to room temperature and treated with 50 ml water. The mixture was extracted with hexane (100 ml) and the organic phase was dried over $Na_2SO_4$; after evaporation of the solvent, the residual oil consisted of pure 10-[1-methyl-1-(3-$^t$butyl-cyclopentadienyl)ethyl]N-methyl-5,10-dihydroindeno[1,2-b]indole. This product, which did not crystallize and did not require any further purification step, was obtained in yield of 93% (5 g), as a mixture of the three isomers due to the presence of the double bonds.

$^1$H-NMR ($CDCl_3$): 7.6–6.9 (m, 8H); 6.62 (m), 6.22 (m), 6.18 (m), 6.08 (m), 6.00 (m), 5.74 (m) total 2H; 4.11 (s), 4.05 (s), 4.02 (s) total 1H; 4.01 (s, 31H); 3.21 (m), 3.19 (m), 3.06 (m) total 2H; 1.50–0.90 group of singlets total 15H.

Example 13

Synthesis of 10-[1-Methyl-1-(3-adamanthyl-cyclopentadienyl) ethyl]N-methyl-5,10-dihydroindeno[1,2-b]indole, Corresponding to Formula (IV) wherein Cp is Like in Ex. 2, A is 3-(1-adamanthyl)-cyclopentadienyl and the Bridging Divalent Radical is $C(CH_3)_2$ (a) Synthesis of 6,6-dimethyl-2-(1-adamanthyl)-fulvene

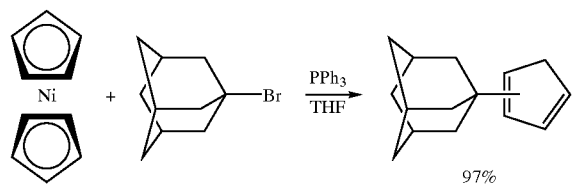

97%

A mixture of nickelocene (12.6 g, 66.7 mmol), 1-bromoadamantane (14.3 g, 66.7 mmol), triphenylphosphine (17.5 g, 66.7 mmol) and dry THF (90 ml) was stirred and heated to the reflux temperature for 10 hours. The solvent was removed by distillation under reduced pressure and the crystalline residue was washed with hot hexane (5×50 ml). Then hexane was evaporated from red extract and the residual deep-red oil was purified by column liquid chromatography (eluent: hexane). Yield 12.9 g (97 %). m.p.=19–21° C.

$^1$H NMR (benzene-$d_6$; 30° C.) δ: 6.64(m); 6.42(m); 6.26(m); 6.13(m); 5.93(m) (Σ=3H, =CH—); 2.92(m, 2H,—$CH_2$—); 2.00(s, 3H); 1.77(s, 6H); 1.61(s, 6H) {Adamantane}.

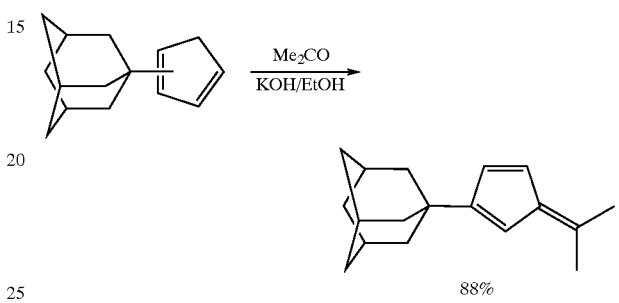

88%

A mixture of KOH (6.05 g, 0.108 mol) and EtOH (50 ml) was degassed. Into well-stirred mixture 1-cyclopentadienyladamantane (7.88 g, 34.7 mmol), obtained as reported above, was added. After 15 minutes at room temperature acetone (3.8 ml, 52 mmol) was added, and the mixture was stirred and heated to the reflux temperature for 1 hour. Then the mixture was poured out into a solution of 85% $H_3PO_4$ (8 ml) in 150 ml of $H_2O$. Yellow precipitate was filtered and washed with $H_2O$ (3×20 ml), EtOH (15 ml), and dried in vacuo. The yield 7.31 g (88%).

$^1$H NMR ($C_6D_6$, 30° C.) δ: 6.69(dd, 1H); 6.60(dd, 1H); 6.24(t, 1H) {—CH=}1.97(bs, 3H); 1.88(bs, 6H); 1.70(bs, 6H) {Adamantane}; 1.87(s, 3H); 1.81(s, 3H) {—$CH_3$}.

(b) Synthesis of 10-[1-methyl-1-(3-adamanthylyclopentadienyl)ethyl]N-methyl-5,10-dihydroindeno[1,2b]indole In a 50 ml bulb were placed 1.80 g (8.3 mmol) of N-methyl-5,10-dihydroindeno[1,2-b]indole prepared in Example 2 and 10 ml THF. The mixture was cooled to −50° C. and subsequently treated with 4.8 ml of BuLi 1.6N (8.3 mmol) in hexane. The resulting solution was allowed to warm to room temperature and subsequently treated with a solution consisting of 2.0 g (8.3 mmol) of 6,6-dimethyl-2-(1-adamanthyl)-fulvene, prepared as described above, in 15 ml of THF. The thus obtained mixture was stirred under reflux for 2 hours; the resulting suspension was cooled to room temperature and treated with 20 ml water. The mixture was extracted with $CH_2Cl_2$ (50 ml) and the organic phase was dried over $Na_2SO_4$; after evaporation of the solvent, the residue was recrystallized from methanol/benzene (2/1), yielding 2.7 g (yield=72%) of a mixture of the three isomers (position of double bonds) of the ligand 10-[1-methyl-1-(3-adamanthyl-cyclopentadienyl)ethyl]N-methyl-5,10-dihydroindeno[1,2-b]indole.

$^1$H-NMR ($CDCl_3$): 7.6–6.9 (m, 8H); 6.60 (m), 6.25 (m), 6.14 (m), 6.09 (m), 5.95 (m), 5.73 (m) total 2H; 4.13 (s), 4.10 (s), 4.07 (s) total 1H; 4.05 (s, 3H); 3.20 (m), 3.18 (m), 3.00 (m) total 2H; 2.1–1,7 group of multiplets total 15H; 1.37 (s), 1.28 (s), 1.25 (s), 0.99 (s), 0.96 (s), 0.94 (s) total 6H.

Example 14

Synthesis of 10-[2-(N-Methyl-5,10-dihydroindeno[1,2-b]indol-10-yl)ethyl]-N-methyl-5,10-dihydroindeno[1,2-b]indole, Corresponding to Formula (IV) Wherein Cp=A Ex. 2 and the Bridging Divalent Radical is $(CH_2)_2$ In a 250 ml bulb were placed 4.38 g (20 mmol) of N-methyl-5,10-dihydroindeno[1,2-b]indole prepared in Example 2 and 50 ml THF. The mixture was cooled to −50° C. and treated with 12.5 ml of BuLi 1.6N (20 mmol) in hexane. The resulting solution was allowed to warm to room temperature, then cooled to −50° C. and finally treated with a solution consisting of 0.85 ml (10 mmol) of 1,2-dibromoethane in 10 ml of THF. The thus obtained mixture was stirred under reflux for 1 hour; the resulting suspension was cooled to room temperature and treated with 1 ml water. It was isolated a white precipitate, which was washed with ether and dried, yielding 3.0 g (yield=60%) of the ligand 10-[2-(N-methyl-5,10dihydroindeno[1,2-b]indol-10-yl)ethyl]-N-methyl-5,10-dihydroindeno[1,2-b]indole.

$^1$H-NMR (CDCl$_3$): 7.6–7.1(m, 16H); 4.05(s, 6H); 3.82(m, 2H); 2.18(m, 2H); 1.83(m, 2H).

Example 15

Synthesis of 10-[1,1-Dimethyl-1-(N-methyl-5,10-dihydroindeno[1,2-b]indol-10-yl)silyl]-N-methyl-5,10-dihydroindeno[1,2-b]indole, Corresponding to Formula (IV) Wherein Cp=A=Ex. 2 and the Bridging Divalent Radical is $Si(CH_2)_2$ In a 100 ml bulb were placed 2.0 g (9 mmol) of N-methyl-5,10-dihydroindeno[1,2-b]indole prepared in Example 2 and 20 ml diethylether. The mixture was cooled to 0° C. and treated with 6 ml of BuLi 1.6N (9 mmol) in hexane. The resulting solution was allowed to warm to room temperature, then cooled to 0° C. and finally treated with a solution consisting of 0.55 ml (4.5 mmol) of Me$_2$SiCl$_2$ in 10 ml of diethylether. The thus obtained mixture was stirred under reflux for 2 hours; the resulting suspension was cooled to room temperature and treated with 20 ml water. It was isolated a white precipitate, which was washed with ether and dried, yielding 1.9 g (yield=85%) of a rac/meso mixture (3:2) of the ligand 10-[1,1-dimethyl-1-(N-methyl-5,10-dihydroindeno[1,2-b]indol-10-yl)silyl]-N-methyl-5,10-dihydroindeno[1,2-b]indole.

$^1$H-NMR (CDCl$_3$): 8.0–7.0 (m, 16H); 4.41 (s, rac-), 4.32 (s, meso) total 2H; 4.16 (s, rac-), 4.13 (s, meso-) total 6H; −0.40 (s, meso-), −0.48 (s, rac-), −0.49 (s, meso-) total 6H.

Example 16

Synthesis of 10-[1-Methyl-1-(cyclopentadienyl)ethyl]N-phenyl-5,10-dihydroindeno[1,2-b]indole, Corresponding to Formula (IV) Wherein Cp is Like in Ex. 3, A is Cyclopentadienyl and the Bridging Divalent Radical is $C(CH_3)_2$ In a 100 ml bulb were placed 4.0 g (15 mmol) of N-phenyl-5,10-dihydroindeno[1,2-b]indole prepared in Example 3 and 20 ml THF. The mixture was cooled to −50° C. and treated with 9.4 ml of BuLi 1.6N (15 mmol) in hexane. The resulting solution was allowed to warm to room temperature and subsequently treated with a solution consisting of 1.6 g (15 mmol) of 6,6-dimethylfulvene in 10 ml of THF. The thus obtained mixture was stirred under reflux for 2 hours; the resulting suspension was cooled to room temperature and treated with 20 ml water. The mixture was extracted with CH$_2$Cl$_2$ (50 ml) and the organic phase was dried over Na$_2$SO$_4$; after evaporation of the solvent, the residue was recrystallized from hexane to yield 2.9 g (yield= 52%) of a mixture of the two isomers (position of double bonds) of the ligand 10-[1-methyl-1-(cyclopentadienyl)ethyl]N-phenyl-5,10-dihydroindeno[1,2-b]indole.

$^1$H-NMR (CDCl$_3$): 7.6–6.9 (m, 13H); 6.89 (m), 6.69 (m), 6.58 (m), 6.48 (m), 6.26 (m), 6.00 (m) total 3H; 4.22 (s), 4.20 (s) total 1H; 3.26 (m), 3.10 (m) total 2H; 1.54 (s), 1.50 (s), 1.03 (s), 1.02 (s) total 6H.

Example 17

Synthesis of 10-[1,1-Dimethyl-1-(N-phenyl-5,10-dihydroindeno[1,2-b]indol-10-yl)silyl]-N-phenyl-5,10-dihydroindeno[1,2-b]indole, Corresponding to Formula (IV) Wherein Cp A Ex. 3 and the Bridging Divalent Radical is $Si(CH_3)_2$ In a 100 ml bulb were placed 4.0 g (15 mmol) of N-phenyl-5,10-dihydroindeno[1,2-b]indole prepared in Example 3 and 50 ml diethylether. The mixture was cooled to 0° C. and treated with 9.4 ml of BuLi 1.6N (15 mmol) in hexane. The resulting solution was allowed to warm to room temperature, then cooled to 0° C. and finally treated with a solution consisting of 0.88 ml (7.5 mmol) of Me$_2$SiCl$_2$ in 10 ml of diethylether. The thus obtained mixture was stirred under reflux for 1 hours; the resulting suspension was cooled to room temperature and treated with 20 ml water. A white precipitate was isolated, washed with ether and dried, yielding 3.6 g (yield=81%) of a rac/meso mixture (1:10) of the ligand 10-[1,1-dimethyl-1-(N-phenyl-5,10-dihydroindeno[1,2-b]indol-10-yl)silyl]-N-phenyl-5,10-dihydroindeno[1,2-b]indole.

$^1$H-NMR (CDCl$_3$): 7.70–7.00 (m, 26H); 4.52 (s, rac-), 4.42 (s, meso-) total 2H; −0.37 (s, meso-), −0.42 (s, rac-), −0.45 (s, meso-) total 6H.

Example 18

Synthesis of 6-[1,1-Dimethyl-1-(N-methyl-5,6-dihydroindeno[2,1-b]indol-6-yl)silyl]-N-methyl-5,6-dihydroindeno[2,1-b]indole, Corresponding to Formula (IV) Wherein Cp=A=Ex. 5 and the Bridging Divalent Radical is $Si(CH_3)_2$ In a 100 ml bulb were placed 2.5 g (11.4 mmol) of N-methyl-5,6-dihydroindeno[2,1-b]indole prepared in Example 5 and 20 ml diethylether. The mixture was cooled to 0° C. and treated with 7.2 ml of BuLi 1.6N (11.4 mmol) in hexane. The resulting solution was allowed to warm to room temperature, then cooled to 0° C. and finally treated with a solution consisting of 0.7 ml (5.7 mmol) of Me2SiCl$_2$ in 10 ml of diethylether. The thus obtained mixture was stirred under reflux for 2 hours; the resulting suspension was cooled to room temperature and treated with 20 ml water. A white precipitate was isolated, washed with ether and dried, yielding 1.7 g (yield=60%) of a rac/meso mixture (5:1) of the target product.

$^1$H-NMR (CDCl$_3$): 7.9–6.8 (m, 16H); 4.02 (s, rac-), 3.62 (s, meso) total 2H; 3.63 (s, meso-), 3.43 (s, rac-) total 6H; 0.06 (s, meso-), −0.38 (s, rac-), 40.42 (s, meso-) total 6H.

Example 19

Synthesis of 6-[1,1-Dimethyl-1-(fluorenyl)silyl][N-methyl-5,6-dihydroindeno[2,1-b]indole, Corresponding to Formula (IV) Wherein Cp=Ex. 5, A=fluorenyl and the Bridging Divalent Radical is Si(CH$_3$)$_2$

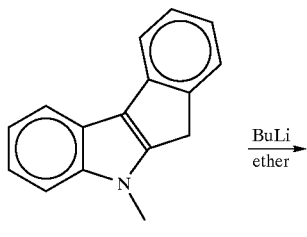

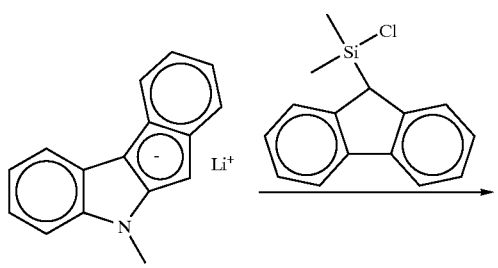

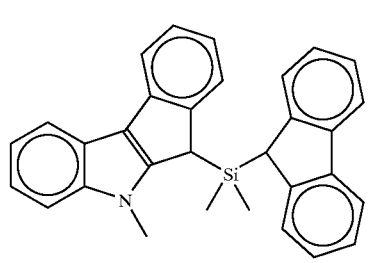

A suspension of 2.19 g (10 mmol) of N-methyl-5,6-dihydroindeno[2,1-b]indole, prepared in Example 5, in 30 ml of ether was treated dropwise with 6.25 ml 1.6N BuLi (10 mmol) in hexane. The resulting deep-yellow solution was cooled to −20° C. and then was treated with a solution of 2.6 g (10 mmol) of fluorenyl-dimethylchlorosilane (prepared as described by K. Patsidis et al., J. Organomet. Chem. 509(1): 63–71, 1996) in 20 ml of ether. The obtained mixture was heated to room temperature, stirred for 1 hour and water was added. The thus obtained precipitate was filtered, washed with water and ethanol, and finally dried, to yield 2.6 g of the target product (yield=59%).

$^1$H-NMR(CDCl$_3$): 8.0–7.1 (group of multiplets, 16H); 4.19(s, 1H); 3.98(s, 1H); 3.58(s, 3H); −0.35(s, 3H); −0.41(s, 3H).

Example 20

Synthesis of 6-[1,1-Dimethyl-1-(2,7-di-t-butyl-fluorenyl)silyl][N-methyl-5,6-dihydroindeno[2,1-b]indole, Corresponding to Formula (IV) Wherein Cp=Ex. 5, A=2,7-di-t-butyl-fluorenyl and the Bridging Divalent Radical is Si(CH$_3$)$_2$

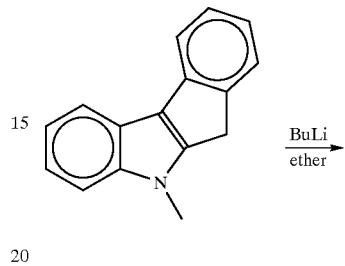

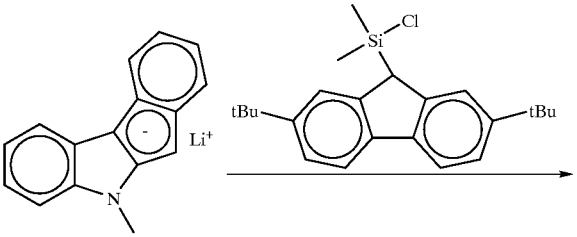

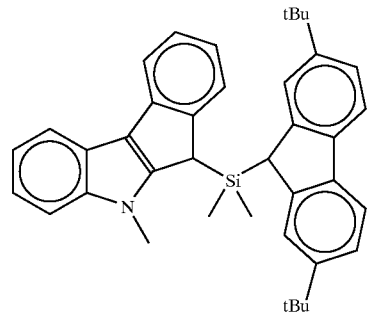

A suspension of 0.65 g (3 mmol) of N-methyl-5,6-dihydroindeno[2,1-b]indole, prepared in Example 5, in 15 ml of ether was treated dropwise with 1.9 ml 1.6N BuLi (3 mmol) in hexane. The resulting deep-yellow solution was cooled to −20° C. and treated with a solution of 1.1 g (3 mmol) of 2,7-di-t-butyl-fluorenyl-dimethylchlorosilane (prepared as described by K. Patsidis et al., J. Organomet. Chem. 509(1): 63–71,1996) in 10 ml of ether. The obtained mixture was heated to room temperature, stirred for 1 hour and water was added. The precipitate was filtered, washed with water and ethanol, and finally dried, thus yielding 0.85 g of the target product (yield=51%).

$^1$H-NMR(CDCl$_3$): 7.86.8 (group of multiplets, 14H); 4.01 (s, 1H); 3.55(s, 1H); 3.40(s, 3H); 1.36(s, 9H); 1.25(s, 9H); −0.29(s, 3H); −0.45(s, 3H).

Example 21

Synthesis of 6-[(N-Methyl-5,6-dihydroindeno[2,1-b]indol-6-yl)methyl]-N-methyl-5,6-dihydroindeno[2,1-b]indole, Corresponding to Formula (IV) Wherein Cp=A=Ex. 5 and the Bridging Divalent Radical is CH$_2$

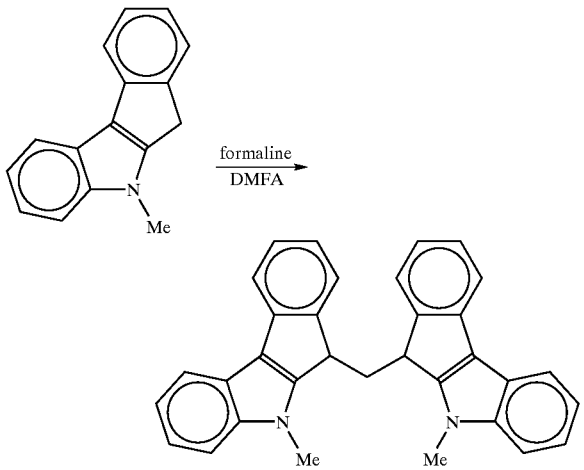

21.9 g (0.1 mol) of N-methyl-5,6-dihydroindeno[2,1-b]indole, prepared in Example 5, and 200 ml of DMFA were placed into a bulb and the resulting mixture was heated under stirring to 50° C. 3.4 g (0.05 mol) of NaOEt were added to the mixture and the resulting solution was stirred for 10 minutes and then treated with 3.8 ml 37% formaline. The resulting mixture was stirred for 2 hours at 75° C.; then it was cooled to room temperature and treated with 5.3 g of NH$_4$Cl. The precipitate was filtered, washed twice with DMFA (30 ml) and with ether, and finally dried thus yielding 20 g of the ligand 6-[(N-methyl-5,6-dihydroindeno[2,1-b]indol-6-yl)methyl]-N-methyl-5,6-dihydroindeno[2,1-b]indole (yield=90%).

$^1$H-NMR (CDCl$_3$): 7.9–7.1 (m, 16H); 4.47 (dd, 2H); 3.61 (s, 6H); 2.23 (dd, 2H).

Example 21-bis

Synthesis of 6-[(N-Methyl-2-methyl-5,6-dihydroindeno[2,1-b]indol-6-yl)methyl]-N-methyl-2-methyl-5,6-dihydroindeno[2,1-b]indole, Corresponding to Formula (IV) Wherein Cp=A=Ex. 9-bis and the Bridging Divalent Radical is CH$_2$

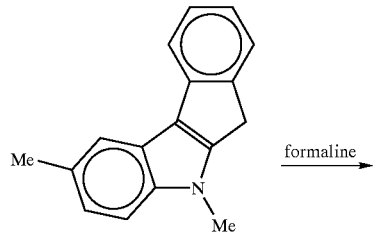

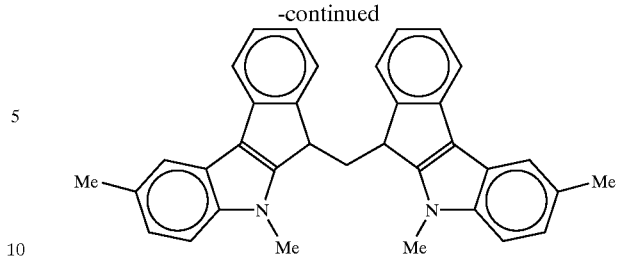

9.32 g (0.04 mol) of N-methyl-2-methyl-5,6-dihydroindeno[2,1-b]indole, prepared in Example 9-bis, and 80 ml of DMFA were placed into a bulb and the resulting mixture was heated under stirring to 50° C. Then 1.36 g (0.02mol) of NaOEt were added; the resulting solution was stirred for 10 minutes and then treated with 1.52 ml 37% formaline. The resulting mixture was stirred for 2 hours at 75° C., then cooled to room temperature and treated with 5 g of NH$_4$Cl. The obtained precipitate was filtered, washed twice with DMFA (15 ml), ethanol and ether, and finally was dried, thus obtaining 9.5 g of 6-[(N-methyl-2-methyl-5,6-dihydroindeno[2,1-b]indol-6-yl)methyl]-N-methyl-2-methyl-5,6-dihydroindeno[2,1-b]indole (yield=99%).

$^1$H-NMR (CDCl$_3$): 7.86(d, 2H); 7.66(d, 2H); 7.63(s, 2H); 7.40(t, 2H); 7.13(m, 4H); 7.02(d, 2H); 4.50(m, 2H); 3.59(s, 6H); 2.52(s, 6H); 2.23(m, 2H).

Example 22

Synthesis of 6-[1,1-Dimethyl-1-(N-phenyl-5,6-dihydroindeno[2,1-b]indol-6-yl)silyl]-3-N-phenyl-5,6-dihydroindeno[2,1-b]indole, Corresponding to Formula (IV) Wherein Cp=A=Ex. 7 and the Bridging Divalent Radical is Si(CH$_3$)$_2$ In a 250 ml bulb were placed 6.45 g (24 mmol) of N-methyl-5,6dihydroindeno[2,1-b]indole prepared in Example 5 and 100 ml diethylether. The mixture was cooled to 0° C. and treated with 15 ml of BuLi 1.6N (24 mmol) in hexane. The resulting solution was allowed to warm to room temperature, then cooled to 0° C. and finally treated with a solution consisting of 1.4 ml (12 mmol) of Me2SiCl$_2$ in 20 ml of diethylether. The thus obtained mixture was stirred under reflux for 1 hours; the resulting suspension was cooled to room temperature and treated with 20 ml water. A white precipitate was isolated, washed with ether and dried, yielding 5.0 g (yield=70%) of pure rac-form of the ligand 6-[1,1-dimethyl-1-(N-phenyl-5,6-dihydroindeno[2,1-b]indol-6-yl)silyl]-N-phenyl-5,6-dihydroindeno[2,1-b]indole (the meso-form was found in the mother solution).

$^1$H-NMR (CDCl$_3$): 7.90–7.00 (m, 26H); 3.60 (s, 2H); −1.03 (s, 6H).

Example 23

Synthesis of 6-[1,1-Dimethyl-1-(N-methyl-2-t-butyl-5,6-dihydroindeno[2,1-b]indol-6yl)silyl]-N-methyl-2-t-butyl-5,6-dihydroindeno[2,1-b]indole, Corresponding to Formula (IV) Wherein Cp=A=Ex 9 and the Bridging Divalent Radical is Si(CH$_3$)$_2$

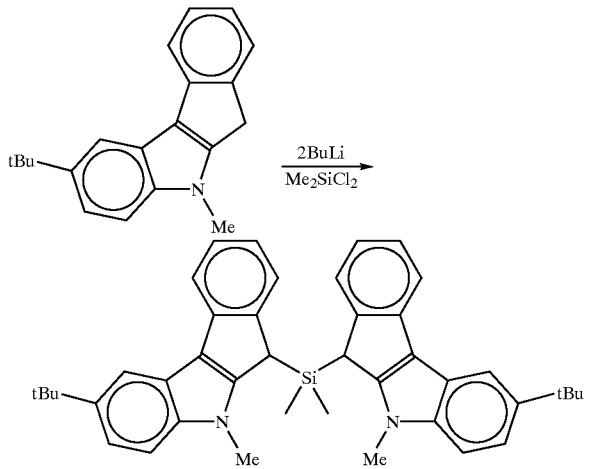

A suspension of 5.5 g (20 mmol) of N-methyl-2-t-butyl-5,6-dihydroindeno[2,1-b]indole, prepared in Example 9, in 50 ml of ether was treated dropwise with 12.5 ml 1.6N BuLi (20 mmol) in hexane. The resulting deep-yellow solution was cooled to −20° C. and then treated with a solution of 1.3 g Me$_2$SiCl$_2$ (10 mmol) in 10 ml of ether. Then obtained mixture was allowed to warm to room temperature and refluxed for 1 hour. The resulting mixture was treated with 100 ml water; the organic layer was collected, washed with water and the solvent was evaporated. The resulting oil was treated with 10 ml of hexane. In some minutes a white precipitate started to form. The obtained precipitate was filtered, washed with hexane and finally dried, thus obtaining the pure rac-form of the target product (2.1 g; yield= 30%).

$^1$H NMR (CDCl$_3$): 7.84(d, 2H); 7.75(d, 2H): 7.66(d, 2H): 7.37(t. 2H): 7.28(dd, 2H); 7.19(d, 2H); 7.15(td, 2H); 4.12(s, 2H); 3.48(s, 6H); 1.42(s, 18H); −0.5(s, 6H).

Example 24

Synthesis of 8-[1,1-Dimethyl-1-(N-methyl-2-methyl-1,8-dihydroindeno[2,1-b]pyrrol-8-yl)silyl]N-methyl-2-methyl-1,8-dihydroindeno[2,1-b]pyrrole, Corresponding to Formula (IV) Wherein Cp=A= Ex.10 and the Bridging Divalent Radical is Si(CH$_3$)$_2$

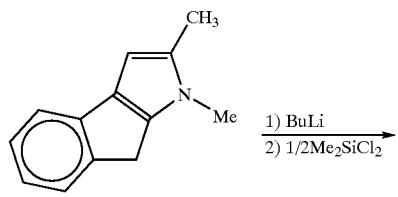

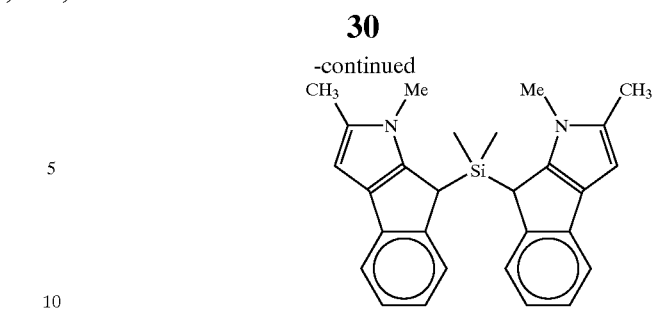

A suspension of 1 g (5.5 mmol) of N-methyl-2-methyl-1,8-dihydroindeno[2,1-b]pyrrole, prepared in Example 10, in 10 ml of ether was cooled to −20° C. and was treated with 3.4 ml 1.6N BuLi in hexane. The resulting mixture was allowed to warm to room temperature; the mixture was then cooled to −50° C. and treated with 0.33 ml (2.7 mmol) Me$_2$SiCl$_2$. The resulting suspension was allowed to warm to room temperature and treated with 10% aqueous NH$_4$Cl solution (50 ml). The precipitate was filtered, washed with ether and finally dried, thus obtaining 0.9 g of 8-[1,1-dimethyl-1-(N-methyl-2-methyl-1,8-dihydroindeno[1,2-b]pyrrol-9-yl)silyl]-N-methyl-2-methyl-1,8-dihydroindeno[1,2-b]pyrrole (yield=77%) as a 1:1=rac:meso mixture.

$^1$H-NMR (CDCl$_3$): 7.55(d,1H); 7.42(d,1H); 7.36(d,1H); 7.26(t,1H); 7.18(t,1H); 7.07(t,1H); 6.94(t,1H); 6.82(d,1H); 6.16(s,1H); 6.11(s,1H); 3.70(s,1H); 3.38 (s,3H); 3.32(s,1H); 3.25(s,3H); 2.33(s,3H); 2.26(s,3H); 0.1(s,1.5H); −0.42(s, 3H); −0.46(s,1.5H).

PREPARATION OF METALLOCENES OF FORMULA (I)

Example 25

Synthesis of Isopropyliden(N-Methyl-5,10-dihydroindeno[1,2-b]indol-10-yl) (cyclopentadienyl) zirconium Dichloride In a 70 ml bulb were placed 3.25 g (10 mmol) of the ligand 10-[1-methyl-1-(cyclopentadienyl)ethyl]N-methyl-5,10-dihydroindeno[1,2-b]indole, prepared in Example 11, and 40 ml diethylether. The obtained mixture was cooled to −50° C. and treated with 14 ml (22 mmol) of BuLi 1.6N in hexane. After two hours, it was observed the precipitation of orange crystals, which were separated, washed with cold diethylether and dried, thus yielding 2.36 g (yield=70%) of the lithium salt of the starting ligand dianion. 1.63 g (7 mmol) of ZrCl$_4$ were suspended in 30 ml of cold CH$_2$Cl$_2$ and the obtained mixture was treated with 2.36 g of the above lithium salt. After vigorous reaction, ZrCl$_4$ dissolved and the solution became violet. After evaporation of the solvent, the obtained complex was recrystallized from toluene, thus yielding 2.2 g of isopropyliden(N-methyl-5,10-dihydroindeno[1,2-b]indol-10-yl)(cyclopentadienyl) zirconium dichloride (yield=60%).

$^1$H-NMR (THF-d$_8$): 8.20 (d,2H); 8.06 (d,H); 7.85 (d,H); 7.50 (d,H); 7.40 (t,H); 7.28 (dd,H); 7.16 (t,H); 6.94 (dd,H); 6.24 (m,1H); 6.10 (m,1H); 5.97 (m,1H); 5.51 (m,1H); 4.19 (s,3H); 2.50 (s,3H); 2.38 (s,3H).

Example 26

Synthesis of Isopropyliden(N-Methyl-5,10-dihydroindeno[1,2-b]indol-10-yl)(3-t-butyl-cyclopentadienyl)zirconium Dichloride In a 70 ml bulb were placed 1.9 g (5 mmol) of the ligand 10-[1-methyl-1-(3-t-butyl-cyclopentadienyl)ethyl]N- methyl-5,10-dihydroindeno[1,2-b]indole, prepared in Example 12, and 20 ml of toluene. The obtained mixture was cooled to −50° C. and treated with 6.25 ml (10 mmol) of BuLi 1.6N in hexane. The resulting solution was allowed to warm to room temperature within 1 hour and then it was treated with 1.16 g (5 mmol) of $ZrCl_4$. The solvent was evaporated and the residue was recrystallized from ether, thus yielding 0.13 g of a mixture about 1:1 of the two isomers meso- and rac- of isopropyliden(N-methyl-5,10-dihydroindeno[1,2-b]indol-10-yl)(3-$^t$butyl-cyclopentadienyl) zirconium dichloride (yield=5%).

$^1$H-NMR ($CD_2Cl_2$): 8.20–7.00 (m,8H); 6.16 (m), 6.00 (m), 5.80 (m), 5.47 (m), 5.39 (m) total 3H; 4.16 (s), 4.15 (s) total 3H; 2.50 (s), 2.49 (s), 2.35 (s), 2.34 (s) total 6H; 1.17 (s), 1.00 (s) total 9H.

Example 27

Synthesis of Isopropyliden(N-Methyl-5,10-dihydroindeno[1,2-b]indol-10-yl)[3-(1-adamanthyl)-cyclopentadienyl]zirconium Dichloride In a 70 ml bulb were placed 2.3 g (5 mmol) of the ligand 10-[1-methyl-1-(3-adamanthylcyclopentadienyl)ethyl]N-methyl-5,10-dihydroindeno[1,2-b]indole, prepared in Example 13, and 20 ml of toluene. The obtained mixture was cooled to −50° C. and treated with 6.25 ml (10 mmol) of BuLi 1.6N in hexane. The resulting solution was allowed to warm to room temperature within 1 hour and then it was treated with 1.16 g (5 mmol) of $ZrCl_4$. The solvent was evaporated and the residue was recrystallized from ether, thus yielding 0.21 g of isopropyliden(N-methyl-5,10-dihydroindeno[1,2-b]indol-10-yl)[3-(1-adamanthyl)-cyclopentadienyl]zirconium dichloride (yield=7%).

Example 28

Synthesis of Isopropyliden(N-phenyl-5,10-dihydroindeno[1,2-b]indol-10-yl)(cyclopentadienyl) zirconium Dichloride In a 70 ml bulb were placed 2.26 g (6 mmol) of the ligand 10-[1-methyl- 1-(cyclopentadienyl)ethyl]N-phenyl-5,10-dihydroindeno[1,2-b]indole, prepared in Example 16, and 20 ml of toluene. The obtained mixture was cooled to −50° C. and treated with 7.5 ml (12 mmol) of BuLi 1.6N in hexane. The resulting solution was allowed to warm to room temperature within 1 hour and then it was treated with 1.4 g (6 mmol) of $ZrCl_4$. The solvent was evaporated and the residue was recrystallized from ether, thus yielding 0.55 g of isopropyliden(N-phenyl-5,10-dihydroindeno[1,2-b]indol-10-yl)(cyclopentadienyl) zirconium dichloride (yield=17%).

$^1$H-NMR ($CD_2Cl_2$): 8.25–7.00 (m,13H); 6.36 (m,1H); 6.29 (m,1H); 5.88 (m,1H); 5.56 (m,1H); 2.57 (s,3H); 2.41 (s,3H).

Example 29

Synthesis of Dimethylsilanediyl-bis(N-phenyl-5,10-dihydroindeno[1,2-b]indol-10-yl)zirconium Dichloride In a 70 ml bulb were placed 4.75 g (8 mmol) of 10-[1, 1-dimethyl-1-(N-phenyl-5,10-dihydroindeno[1,2-b]indol-10-yl]-silyl]-N-phenyl-5,10-dihydroindeno[1,2-b]indole, prepared in Ex. 17, and 40 ml of ether. The obtained mixture was cooled to −50° C. and treated with 12.5 ml (2 mmol) of BuLi 1.6N in hexane. In the period of two hours, the precipitation of yellow crystals is observed; said crystals were isolated, washed with cold ether and dried, yielding 2.9 g (60%) of the lithium salt of the ligand dianion.

1.12 g (4.8 mmol) of $ZrCl_4$ were suspended in 30 ml of cold $CH_2Cl_2$ and the obtained mixture was treated with 2.9 g (4.8 mmol) of the lithium salt obtained as described above. After vigorous reaction, $ZrCl_4$ dissolved and the solution became dark violet. The solution was concentrated to 5 ml. and cooled to −50° C. A crystalline solid was isolated, washed with cold $CH_2Cl_2$ and dried, thus yielding 2.35 g of dimethylsilanediyl-bis(N-phenyl- 5,10-dihydroindeno[1,2-b]indol-10-yl) zirconium dichloride (yield=65%).

Example 30

Synthesis of Dimethylsilanediyl-bis(N-methyl-5,6-dihydroindeno[2,1-b]indol-6-yl)zirconium Dichloride In a 70 ml bulb were placed 2.48 g (5 mmol) of 10-[1, 1-dimethyl-1-(N-methyl-5,10-dihydroindeno[1,2-b]indol-10-yl)-silyl]N-methyl-5,10-dihydroindeno[1,2-b]indole, prepared in Example 18, and 20 ml of toluene. The obtained mixture was cooled to −50° C. and treated with 6.25 ml (10 mmol) of BuLi 1.6N in hexane. The resulting solution was allowed to warm to room temperature within 1 hour and then it was treated with 1.16 g (5 mmol) of $ZrCl_4$. The resulting yellow crystals were separated, washed with toluene and dried, thus yielding 0.39 g of dimethylsilanediyl-bis(N-methyl-5,6-dihydroindeno[2,1-b]indol-6-yl)zirconium dichloride (yield=12%) in the form of the rac-isomer.

$^1$H-NMR ($CD_2Cl_2$): 7.6–6.9 (m,26H); 3.7 (s,6H); 2.37 (s,6H).

Example 31

Synthesis of Dimethylsilanediyl-(fluorenyl)(N-methyl-5,6-dihydroindeno[2,1-b]indol-6-yl) zirconium Dichloride

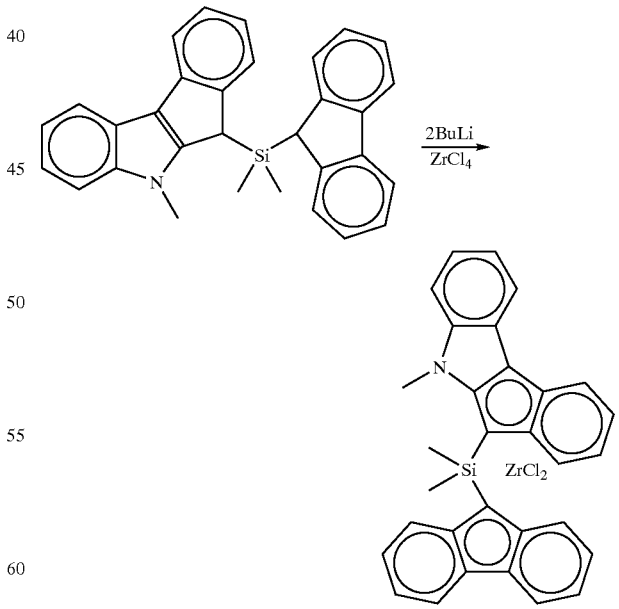

A suspension of 2.2 g (5 mmol) of 6-[1,1-dimethyl-1-(fluorenyl)silyl][N-methyl- 5,6-dihydroindeno[2,1-b]indole, prepared in Example 19, in 40 ml of ether was treated with 6.25 ml 1.6N BuLi (10 mmol) in hexane. The resulting solution was cooled to −50° C. and treated with 1.16 g (5 mmol) of ZrCl$_4$. The obtained mixture was allowed to warm to room temperature and then stirred for 2 hours at room temperature. The thus obtained orange precipitate was filtered, washed with THF and ether, and finally dried, thus yielding 2.1 g of dimethylsilanediyl-(fluorenyl)(N-methyl-5,6-dihydroindeno[2,1-b]indol-6-yl) zirconium dichloride (yield=70%).

Example 32

Synthesis of Methylen-bis(N-methyl-5,6-dihydroindeno[2,1-b]indol-6-yl)zirconium Dichloride In a 100 ml bulb were placed 2.25 g (5 mmol) of 6-[(N-methyl-5,6-dihydroindeno[2,1-b]indol-6-yl)methyl]-N-methyl-5,6-dihydroindeno[2,1-b]indole, prepared in Example 21, and 40 ml of diethylether. The obtained mixture was cooled to −50° C. and treated with 6.25 ml (10 mmol) of BuLi 1.6N in hexane. The starting ligand dissolved and the corresponding white dilithium salt started to precipitate; the precipitate was isolated, washed with diethylether and dried, thus yielding 1.8 g of said dilithium salt (yield=78%).

0.9 g of ZrCl$_4$ (3.9 mmol) was suspended in 30 ml of cold CH$_2$Cl$_2$ and the obtained mixture was treated with 1.8 g (3.9 mmol) of the above dilithium salt. ZrCl$_4$ dissolved and a red crystalline solid precipitated; the precipitate was isolated, washed with cold CH$_2$Cl$_2$ and dried, thus yielding 0.82 g of methylen-bis(N-methyl-5,6-dihydroindeno[2,1-b]indol-6-yl) zirconium dichloride (yield=33%).

Example 32-bis

Synthesis of Methylen-bis(N-methyl-2-methyl-5,6-dihydroindeno[2,1-b]indol-6-yl)zirconium Dichloride

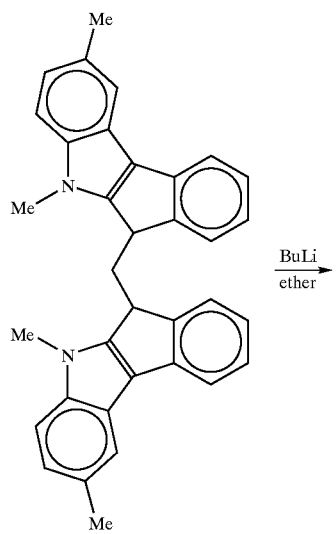

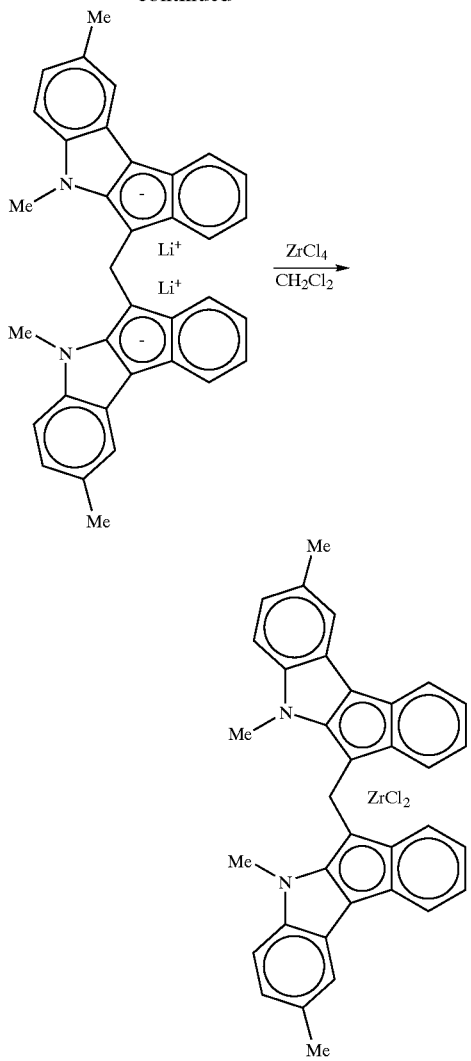

A suspension of 3 g (6.67 mmol) of 6-[(N-methyl-2-methyl-5,6-dihydroindeno[2,1-b]indol-6-yl)methyl]-N-methyl-2-methyl-5,6-dihydroindeno[2,1-b]indole, prepared in example 21-bis, in 60 ml of ether was treated with 10 ml 1.6N BuLi (16 mmol) in hexane and stirred within 3 h. The resulting yellow suspension, containing the dilithium salt of the ligand, was isolated by filtration, washed twice with ether and dried.

The obtained product was dissolved in 50 ml of dichloromethane at −50° C. and the resulting yellow solution was treated with 1.5 g (6.67 mmol) of ZrCl$_4$. The mixture was allowed to warm to room temperature under stirring for 3 hours. The inorganic by-products were filtered, and the solution was evaporated to 5 ml. The red crystalline precipitate was isolated by filtration, washed with cold dichloromethane and dried, thus obtaining 0.85 g of the target product(yield=20%).

Example 33

Synthesis of Dimethylsilanediyl-bis(N-phenyl-5,6-dihydroindeno[2,1-b]indol-6-yl)zirconium Dichloride In a 70 ml bulb were placed 5.94 g (10 mmol) of 6-[1,1-dimethyl-1-(N-phenyl-5,6-dihydroindeno[2,1-b]

indol-6-yl)-silyl]-N-phenyl-5,6dihydroindeno[2,1-b]indole, prepared in Ex. 22, and 40 ml of diethylether. The obtained mixture was cooled to −50° C. and treated with 14 ml (22 mmol) of BuLi 1.6N in hexane. In the period of two hours, the precipitation of white crystals was observed; said crystals were isolated, washed with cold diethylether and dried, yielding 3.6 g of the lithium salt of the ligand dianion (yield=60%).

1.4 g (6 mmol) of $ZrCl_4$ were suspended in 30 ml of cold $CH_2Cl_2$ and the mixture was treated with 3.6 (6 mmol) of the lithium salt obtained above. After vigorous reaction, $ZrCl_4$ dissolved and the solution became orange. The solvent was evaporated and the complex was recrystallized from toluene, thus giving dimethylsilanediyl-bis(N-phenyl-5,6-dihydroindeno [2,1-b]indol-6-yl)zirconium dichloride in very high yields.

Example 34

Synthesis of Dimethylsilanediyl-bis(N-methyl-2-t-butyl-5,6-dihydroindeno[2,1-b]indol-6-yl)zirconium Dichloride

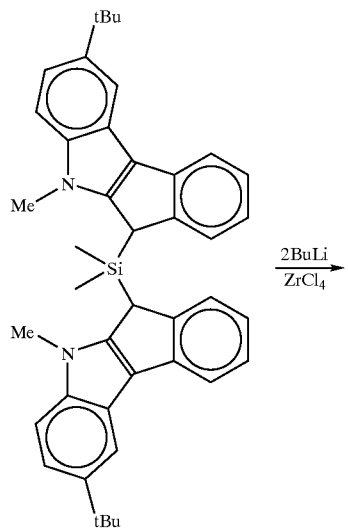

A solution of 1.36 g (2 mmol) of the ligand 6-[1,1-dimethyl-1-(N-methyl-2-t-butyl-5,6-dihydroindeno[2,1-b]indol-6-yl)silyl]-N-methyl-2-t-butyl-5,6-dihydroindeno[2, 1-b]indole, prepared in Example 23, in 40 ml of ether was treated with 2.5 ml 1.6N BuLi (4 mmol) in hexane. The resulting solution was cooled to −50° C. and treated with 0.47 g (2 mmol) of ZrCl4. The mixture was allowed to warm to room temperature and stirred for 2 hours at room temperature. The thus obtained yellow precipitate was filtered, washed with ether and finally dried, thus obtaining 0.83 g of the target product (yield=50%).

Example 35

Synthesis of bis(N-Methyl-5,6-dihydroindeno[2,1-b] indol-6-yl)zirconium Dichloride In a 100 ml bulb were placed 2.19 g (10 mmol) of N-methyl-5,6-dihydroindeno[2,1-b]indole, prepared in Example 5, and 30 ml of diethylether. The obtained mixture was cooled to 0° C. and treated with 6.25 ml (10 mmol) of BuLi 1.6N in hexane. The resulting solution was cooled to −50° C. and treated with 1.16 g (5 mmol) of $ZrCl_4$. The resulting mixture was allowed to warm to room temperature and maintained under continuous stirring for 12 hours. A yellow precipitate was isolated, washed with diethylether and recrystallized from $CH_2Cl_2$, thus obtaining 1.0 g of N-methyl-5,6-dihydroindeno[2,1-b]indole yield=33%), in the form of yellow crystals. The mother solution was evaporated and the resulting solid was recrystallized from toluene, thus giving a total yield of 1.2 g (yield=40%).

Example 36

Synthesis of bis(N-Phenyl-5,10-dihydroindeno[1,2-b]indol-10-yl)zirconium Dichloride In a 100 ml bulb were placed 2.81 g (10 mmol) of N-phenyl-5,10-dihydroindeno[1,2-b]indole, prepared in Example 3, and 30 ml of diethylether. The obtained mixture was cooled to 0° C. and treated with 6.25 ml (10 mmol) of BuLi 1.6N in hexane. The resulting solution was cooled to −50° C. and treated with 1.16 g (5 mmol) of $ZrCl_4$. The obtained mixture was allowed to warm to room temperature and maintained under continuous stirring for 2 hours.

A red precipitate was isolated, washed with diethylether and dried; the resulting solid was washed with 50 ml of $CH_2Cl_2$ and the resulting solution was concentrated up to 5 ml. Red crystals were isolated, washed with cold $CH_2Cl_2$ and dried, thus yielding 1.3 g of bis(N-phenyl-5,10-dihydroindeno[1,2-b]indol-10-yl)zirconium dichloride (yield=36%).

Example 37

Synthesis of Dimethylsilanediyl-bis(N-methyl-2-methyl-1,8-dihydroindeno[2,1-b]pyrrol-8-yl) zirconium Dichloride

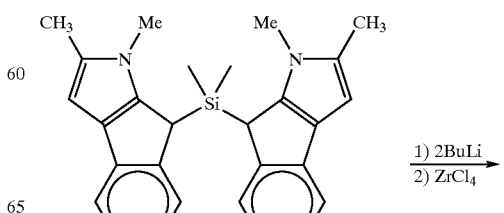

-continued

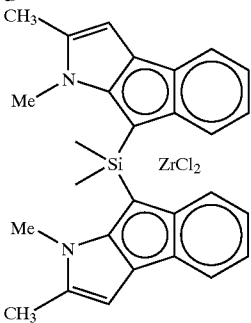

A suspension of 0.9 g (2.1 mmol) of the ligand prepared in Example 23 in 20 ml of ether was treated with 2.7 ml 1.6N BuLi in hexane, at room temperature. The resulting mixture was stirred for 3 hours and then treated with 0.49 g (2.1 mmol) of $ZrCl_4$. The red precipitate that formed was filtered and recrystallized from dichloromethane, thus giving 0.3 g of the target compound (yield=25%).

POLYMERIZATION TESTS

Methylalumoxane (MAO)

A commercial product (by Schering) was used in solution of 10% by weight in toluene.

Tris-(2,4,4-trimethyl-pentyl)alumoxane (TIOAO)

3.45 ml of a TIOA solution (1M in hexane) were added at room temperature to 5 ml of toluene, previously deoxygenated and distilled over triisobutylaluminum. 0,031 ml of water were then added, at room temperature, with a syringe and the resulting solution was stirred for 10 minutes at room temperature.

Tris-(2,4,4-trimethyl-pentyl)aluminum (TIOA)

A commercial sample (by Witco) was used diluted to a 1M solution in the indicated solvent.

Tris(2-methyl-propyl)aluminum (TIBA)

A commercial product available from Witco was used.

Preparation of the catalyst solution

The catalyst solution was prepared, in a glass flask treated with $N_2$ at 90° C. for 3 hours, by dissolving a known amount of a metallocene according to the present invention in toluene, then transferring an aliquot of this solution into a toluene solution containing the desired amount of cocatalyst, obtaining a clear solution which was stirred for 5 minutes at room temperature and then injected into the autoclave at the polymerization temperature in the presence of the monomer.

ETHYLENE POLYMERIZATION (HDPE)

Example 38

The catalyst solution prepared as described above, containing a metallocene catalyst of the invention, as reported in Table 1, and methylalumoxane (MAO) as cocatalyst, was fed into a 4-liters steel autoclave (1-liter autoclave with the ziconocene of Ex. 32), equipped with anchor stirrer and treated with $N_2$ at 90° C. for 3 hours, containing 1.6 l of hexane (0.51 with Ex. 32) and 1.0 mmol of TIBAL (2.0 mmol with Ex. 32), at about 20° C. The autoclave temperature was raised to 80° C. and 10 bar of ethylene were supplied. Polymerization was effected for 1 hour, keeping the temperature and ethylene pressure constant.

Polymerization was discontinued by instantaneous degassing of the autoclave and, after cooling to 20° C., the obtained slurry of polymer was discharged and dried in an oven in nitrogen atmosphere, at the temperature of 80° C.

The experimental parameters and quantities, as well as polymerization data are reported in Table 1.

Example 39

A 200 ml glass autoclave, provided with magnetic stirrer, temperature indicator and feeding line for the ethylene, was purified and fluxed with ethylene at 35° C. At room temperature were introduced 90 ml of hexane. The catalytic system was prepared separately in 10 ml of hexane, by consecutively introducing the cocatalyst (the corresponding aluminum alkyl and water, in a ratio $Al/H_2O=2.1$, when necessary) indicated in Table 1-bis, and after 5 minutes of stirring, the metallocene solved in a the lowest possible amount of toluene, as reported in Table 1-bis.

After 5 minutes stirring, the solution was introduced into the autoclave under ethylene flow, the reactor was closed, the temperature risen to 80° C. and pressurized to 4.6 barg. The total pressure was kept constant by feeding ethylene.

After the polymerization time reported in Table 1-bis, the polymerization was stopped by cooling, degassing the reactor and the introduction of 1 ml of methanol. The achieved polymer was washed with acidic methanol, than with methanol and dried in oven at 60° C. under vacuum.

The polymerization conditions and the characterization data of the obtained polymers are indicated in Table 1-bis.

Example 40

Influence of Temperature

In order to evaluate the influence of temperature on the activity of the metallocene according to the present invention, ethylene polymerization was carried out using the metallocene prepared in Example 30 with MAO as cocatalyst, following the procedure reported in Example 38, but varying the temperature of polymerization. Polymerization data are reported in Table 2.

Example 41

Influence of Hydrogen

In order to evaluate the influence of hydrogen on the molecular weight of the obtained polymers, ethylene polymerization was carried out using the metallocene prepared in Example 30 with MAO as cocatalyst, following the procedure reported in Example 38, with the only difference of introducing hydrogen in the reaction mixture. Polymerization data are reported in Table 3.

The obtained results confirm that the metallocenes according to the present invention are sensitive to hydrogen as a molecular weight regulator; this fact is unexpected in the light of the polymerization results reported in the cited European patent application EP 0 604 908 where hydrogen, even when used in relevant amounts, has no effect on the molecular weight of the obtained polymers. Therefore, with the metallocenes of the invention it is possible to regulate the molecular weight of the final polymer, maintaining at the same time intrinsic viscosity values of interest.

The use of hydrogen in polymerization reactions carried out with the catalysts according to the invention, even if in low amounts so that the yields of the process are not negatively affected, makes it possible to regulate the molecular weight of the obtained polymers up to Tm values of practical interest.

Example 42

Influence of the Cocatalyst

In order to test the activity of the metallocenes according to the present invention with different cocatalysts, ethylene polymerization was carried out using the metallocene prepared in Example 30 with MAO or TIOAO as cocatalyst, following the polymerization procedure described in Example 38. Polymerization data are reported in Table 4.

The obtained results confirm that the metallocenes according to the present invention are very active with various cocatalysts.

Example 43

Influence of the Al/Zr Ratio

In order to test the influence of the Al/Zr ratio on the activity of the metallocenes according to the present invention, ethylene polymerization was carried out using the metallocene prepared in Example 30 with MAO as cocatalyst, following the polymerization procedure described in Example 38. Polymerization data are reported in Table 5.

The obtained results confirm the fact that the metallocenes according to the present invention are very active even when used in very low Zr/Al ratios.

ETHYLENE COPOLYMERIZATION (LLDPE)

Example 44

Ethylene/1-butene Copolymerization

The catalyst solution prepared as described above, containing the metallocene of example 30 or 33, and MAO or TIOAO as cocatalyst, was fed into a 4-liters steel autoclave, equipped with anchor stirrer and treated with $N_2$ at 90° C. for 3 hours, containing 1.6 l of hexane and 1.0 mmol of TIBAL, at about 20° C. The autoclave temperature was raised to the desired value and the quantities of ethylene, 1-butene and hydrogen indicated in Table 6 were introduced under anhydrous nitrogen atmosphere. In trials conducted with the metallocene of Ex. 30 1-butene (g) was introduced into the autoclave at the beginning, while in trials with Ex. 33 1-butene (%) was charged together with ethylene. Polymerization was carried out for the reaction times reported in Table 6, under continuous stirring, keeping the temperature and the pressure of ethylene and hydrogen constant.

Polymerization was discontinued by instantaneous degassing of the autoclave and, after cooling to 20° C., the obtained slurry of polymer was discharged and dried in an oven in nitrogen atmosphere, at the temperature of 80° C.

The polymerization conditions and yields are reported in Table 6. The data of the obtained copolymers are reported in Table 7, following the same order of Table 6.

Example 45

Ethylene/1-hexene Copolymerization

A 200 ml glass autoclave, provided with magnetic stirrer, temperature indicator and feeding line for the ethylene, was purified and fluxed with ethylene at 35° C. At room temperature were introduced 90 ml of heptane and the amount of 1-hexene reported in Table 7-bis.

The catalytic system was prepared separately in 10 ml of heptane by consecutively introducing MAO and the metallocene indicated in Table 7-bis solved in the lowest possible amount of toluene (the low amount as possible).

After 5 minutes stirring, the solution, was introduced into the autoclave under ethylene flow, the reactor was closed, the temperature risen to 70° C. and pressurized to 4.6 barg. The total pressure was kept constant by feeding ethylene.

After the reaction time reported in Table 7-bis, the polymerization was stopped by cooling, degassing the reactor and the introduction of 1 ml of methanol. The achieved polymer was washed with acidic methanol, than with methanol and dried in oven at 60° C. under vacuum. The polymerization conditions and yields are reported in Table 7-bis. The data of the obtained copolymers are reported in Table 7-ter.

ETHYLENEIPROPYLENE COPOLYMERIZATION

Example 46

The copolymerization was carried out by continuously supplying the monomer mixture at a constant flow rate in a 250 ml glass reactor equipped with a stirring and a thermometer. The cocatalyst was prepared by dissolving 3.45 ml of TIOA (1M in hexane) in 5 ml of toluene, then adding 0.031 ml of water and then stirring the solution for 10 minutes. The cocatalyst was then added to a nitrogen purged reactor containing 100 ml of toluene. The reactor was put into a thermostated bath and, when the reaction temperature of 50° C. was reached, a mixture of ethylene and propylene, containing 60% w of ethylene, was supplied continuously, at a total pressure of 80 mmHg and a flow rate of 50 l/h.

3.45 $\mu$mol of a metallocene according to the present invention, as reported in Table 8, dissolved in 5 ml of toluene, were added to start polymerization, having therefore a ratio Al/Zr of 1000 and a ratio $Al/H_2O$ of 2. After 15 minutes the polymerization was stopped by adding 1 ml of methanol and the copolymer was coagulated in acidulated methanol, then filtered and dried under vacuum. Yields and characteristics of the obtained copolymers are reported in Table 8.

The obtained results demonstrate a good activity of the metallocenes of the invention in ethylene/propylene copolymerization.

PROPYLENE POLYMERIZATION

Example 47

200 g of propylene were charged in a 1 l jacketed stainless-steel autoclave, equipped with magnetically driven stirrer and a 35 ml stainless steel vial, connected to a thermostat for temperature control, previously purified by washing with a TIBA solution in hexane and dried at 50° C. in a stream of propylene, then cooled to room temperature.

The autoclave was then thermostated at the polymerization temperature indicated in Table 9. The catalyst mixture was prepared by adding the amount of zirconocene dichloride indicated in Table 9 to a MAO solution in toluene, obtaining a solution which was stirred for 10 minutes at room temperature and then injected into the autoclave by means of nitrogen pressure through the stainless-steel vial, at the polymerization temperature.

The polymerization was carried out at constant temperature for 1 hour and then it was quenched with carbon monoxide. After venting the unreacted monomer and cooling the reactor to room temperature, the polymer was dried under reduced pressure, at 60° C. The polymerization data are reported in Table 9, while the characterization data of the obtained polymers are reported in Table 10.

The obtained results demonstrate that, by suitably changing molecular symmetry, the metallocenes according to the present invention may give propylene polymers having high isotacticity (mmmm pentad content higher than 90%) or may give syndiotactic polypropylene (rrrr pentad content).

TABLE 1

| Example | Metallocene (g) | Al/Zr (mol) | Yield (g) | Activity met (kg/g$_{met}$·h) | Activity Zr (Kg/g$_{Zr}$·h) | η (dl/g) |
|---|---|---|---|---|---|---|
| Ex. 25 | 0.002 | 1900 | 200 | 100 | 530 | 1.38 |
| Ex. 26 | 0.002 | 2200 | 126 | 63 | 375 | 4.27 |
| Ex. 27 | 0.002 | 2500 | 118 | 59 | 402 | 2.88 |
| Ex. 28 | 0.002 | 2200 | 85 | 42 | 265 | 2.15 |
| Ex. 29 | 0.002 | 1600 | 190 | 95 | 810 | 4.75 |
| Ex. 29 | 0.002 | 3100 | 180 | 90 | 770 | 6.1 |
| Ex. 30 | 0.0003 | 8700 | 180 | 600 | 4310 | 2.98 |
| Ex. 32 | 0.0003 | 200 | 25.9 | 86.3 | 578 | 4.2 |
| Ex. 33 | 0.0005 | 9900 | 170 | 340 | 2892 | 4.79 |

TABLE 1 bis

| Ex. | Metalloc. (mg) | Cocatalyst type | Cocatalyst (mmol) | Al/Zr (mol) | Time (min) | Yield (g) | Activity (Kg/g$_{Zr}$·h) | η (dl/g) |
|---|---|---|---|---|---|---|---|---|
| Ex. 29 | 0.30 | TIOA/H$_2$O | 0.4 | 1000 | 3 | 0.2 | 113.9 | 16.1 |
| Ex. 29 | 0.15 | MAO | 0.2 | 1000 | 6 | 0.43 | 244.9 | >13 |
| Ex. 32 | 0.13 | MAO | 0.22 | 1000 | 2 | 0.8 | 1236.2 | n.d. |
| Ex. 32 | 0.09 | MAO | 0.15 | 1000 | 10 | 2.39 | 1066.9 | 5.75 |
| Ex. 32 | 0.10 | TIOAO/MAO 9:1 | 0.17 | 1000 | 2 | 1.68 | 3374.9 | n.d. |
| Ex. 32 | 0.05 | TIOAO/MAO 9:1 | 0.09 | 1100 | 4 | 1.47 | 2953.0 | n.d. |
| Ex. 33 | 0.20 | MAO | 0.26 | 1000 | 2 | 1.11 | 1422.1 | 11.29 |
| Ex. 32* | 0.10 | MAO | 0.179 | 1100 | 15 | 1.94 | 519.6 | n.d. |
| Ex. 32* | 0.05 | TIOA/MAO 9:1 | 0.087 | 1100 | 15 | 3.15 | 1687 | n.d. |
| Ex. 32* | 0.05 | TIBA/MAO 9:1 | 0.085 | 1100 | 15 | 4.3 | 2030 | n.d. |

*The procedure described in Example 39 was followed, with the differences that a 300 ml autoclave with a mechanical stirrer was used, with 150 ml heptane as solvent, at a Ptot of 4 barg.

Example 48

Influence of Al/Zr Ratio

In order to test the influence of the Al/Zr ratio on the activity of the metallocenes according to the present invention, propylene polymerization was carried out using the metallocene prepared in Example 30 with MAO as cocatalyst, at the temperature of 60° C., for a period of 1 hour, following the polymerization procedure described in Example 47, with the difference that AliBu$_3$ (1 mmol) was charged in the reactor before charging the catalyst mixture. Polymerization data are reported in Table 11.

The obtained results confirm the fact that the metallocenes according to the present invention are very active even when used in very low Zr/Al ratios.

Example 49

Influence of Temperature

In order to evaluate the influence of temperature on the activity of the metallocene according to the present invention, propylene polymerization was carried out using the metallocene prepared in Example 30 with MAO as cocatalyst, following the polymerization procedure described in Example 47, but varying the temperature of polymerization. AliBu$_3$ (1 mmol) was charged in the reactor before charging the catalyst mixture. Polymerization data are reported in Table 12.

TABLE 2

| Metallocene (g) | Al/Zr (mol) | T (° C.) | Activity met (kg/g$_{met}$·h) | Activity Zr (Kg/g$_{Zr}$·h) | η (dl/g) |
|---|---|---|---|---|---|
| 0.0003 | 8700 | 60 | 740 | 5318 | 6.2 |
| 0.0003 | 8700 | 70 | 670 | 4815 | 4.67 |
| 0.0003 | 8700 | 80 | 600 | 4312 | 2.98 |

TABLE 3

| Metallocene (g) | Al/Zr (mol) | Hydrogen (ml) | Activity met (kg/g$_{met}$·h) | Activity Zr (Kg/g$_{Zr}$·h) | η (dl/g) |
|---|---|---|---|---|---|
| 0.0003 | 8700 | 0 | 600 | 4312 | 2.98 |
| 0.0003 | 8700 | 200 | 400 | 2875 | 2.47 |
| 0.0003 | 8700 | 300 | 276 | 1984 | 2.15 |
| 0.0003 | 8700 | 450 | 240 | 1725 | 2.12 |

TABLE 4

| Metallocene (g) | Cocatalyst | Al/Zr (mol) | Activity met (kg/g$_{met}$·h) | Activity Zr (Kg/g$_{Zr}$·h) | η (dl/g) |
|---|---|---|---|---|---|
| 0.0003 | MAO | 8700 | 600 | 4312 | 2.98 |
| 0.0003 | MAO | 17400 | 533 | 3830 | 2.54 |
| 0.0003 | TIOAO | 18300 | 630 | 4530 | 4.8 |

TABLE 5

| Metallocene (g) | Al/Zr (mol) | Yield (g) | Activity met (kg/g$_{met}$ · h) | Activity Zr (Kg/g$_{Zr}$ · h) | η (dl/g) |
|---|---|---|---|---|---|
| 0.0003 | 8700 | 180 | 600 | 4312 | 2.98 |
| 0.0009 | 125 | 190 | 210 | 1511 | 3.97 |
| 0.001 | 50 | 190 | 190 | 1368 | 3.76 |
| 0.001 | 15 | 150 | 150 | 1080 | 5.05 |

TABLE 6

| Ex. | Metallocene (g) | Cocat | Al/Zr (mol) | Time (h) | T °C. | Ethylene (bar) | butene | Activity kg/g$_{met}$ · h | Activity Kg/g$_{Zr}$ · h |
|---|---|---|---|---|---|---|---|---|---|
| Ex. 30 | 0.0005 | TIOAO | 8700 | 2 | 80 | 10 | 60 g | 220 | 1582 |
| Ex. 30 | 0.0002 | MAO | 8700 | 2 | 70 | 10 | 60 g | 590 | 4238 |
| Ex. 30 | 0.0005 | MAO | 8700 | 2 | 70 | 10 | 15 g | 220 | 1582 |
| Ex. 33 | 0.0005 | MAO | 9900 | 2 | 70 | 10 | 6% | 280 | 2391 |
| Ex. 33 | 0.0005 | MAO | 9900 | 1.1 | 70 | 10.1 | 8% | 250 | 2135 |

TABLE 7

| Example | Tm (° C.) | density (g/ml) | 1-butene (% w) | Xylene insoluble (% w) | η (dl/g) |
|---|---|---|---|---|---|
| Ex. 30 | 120.4 | 0.919 | 7 | 99.8 | 2.75 |
| Ex. 30 | 106 | 0.904 | n.d. | 92.9 | 1.96 |
| Ex. 30 | n.d. | n.d. | n.d. | 98.9 | 3 |
| Ex. 33 | n.d. | n.d. | n.d. | 99.8 | 1.62 |
| Ex. 33 | n.d. | n.d. | n.d. | 99.9 | 1.82 |

TABLE 7 bis

| Ex. | Metallocene (mg) | Cocat (mmol) | Al/Zr (mol) | 1-hexene (ml) | Time (min) | Yield (g) | Activity Kg/g$_{Zr}$ · h |
|---|---|---|---|---|---|---|---|
| Ex. 30 | 0.15 | 0.247 | 1100 | 2 | 10 | 3.28 | 942.0 |
| Ex. 32 | 0.13 | 0.23 | 1100 | 10 | 10 | 4.03 | 1245.5 |
| Ex. 32 | 0.08 | 0.139 | 1100 | 2 | 10 | 2.24 | 1125.0 |

TABLE 7-ter

| Example | 1-hexene (% w) | Tm (° C.) | η (dl/g) | H (J/g) |
|---|---|---|---|---|
| Ex. 30 | 21.6 | 78.5 | 2.43 | 54.7 |
| Ex. 32 | 27.9 | 68.6 | 1.16 | 47 |

TABLE 8

| Example | Yield (g) | Activity (kg/g$_{Zr}$ · h) | Ethylene (% w) | r$_1$ · r$_2$ | η (dl/g) |
|---|---|---|---|---|---|
| Ex. 25 | 2.9 | 9.4 | 71.5 | 0.43 | 0.82 |
| Ex. 26 | 0.62 | 2.0 | 83.7 | 0.86 | ≅2 |
| Ex. 27 | 0.37 | 1.2 | ≅80 | n.d. | 3.14 |
| Ex. 28 | 3.45 | 10.9 | 69.5 | 0.41 | 0.96 |
| Ex. 30 | 0.8 | 2.5 | 83.9 | 0.29 | 1.13 |
| Ex. 32 | 5.4 | 16.0 | n.d. | n.d. | n.d. |
| Ex. 34 | 2.54 | 8.1 | 77.8 | 0.34 | 1.30 |
| Ex. 37 | 2.94 | 9.4 | 77.2 | n.d. | 1.21 |

TABLE 9

| Ex. | Metallocene (g) | Al/Zr mol | T °C. | Yield g | Activity kg/g$_{met}$ · h | Activity Kg/g$_{Zr}$ · h | η dl/g |
|---|---|---|---|---|---|---|---|
| Ex. 25 | 0.001 | 5000 | 50 | 7 | 7.0 | 6.4 | n.d. |
| Ex. 25 | 0.002 | 3000 | 70 | 8 | 4.0 | 3.7 | n.d. |
| Ex. 26 | 0.002 | 3000 | 70 | 30.6 | 15.3 | 15.0 | 0.4 |
| Ex. 27 | 0.002 | 3000 | 50 | 37 | 18.5 | 18.2 | 0.47 |

TABLE 9-continued

| Ex. | Metallocene (g) | Al/Zr mol | T °C. | Yield g | Activity kg/g$_{met}$ · h | Activity Kg/g$_{Zr}$ · h | η dl/g |
|---|---|---|---|---|---|---|---|
| Ex. 28 | 0.002 | 3000 | 70 | 19 | 9.5 | 9.2 | 0.48 |
| Ex. 30* | 0.002 | 2800 | 60 | 164 | 82.0 | 81.8 | 0.23 |
| Ex. 32 | 0.003 | 3000 | 60 | 15 | 5.0 | 33.5 | 0.23 |
| Ex. 37 | 0.002 | 3000 | 50 | 7.6 | 3.8 | 24.5 | n.d. |

*AliBu$_3$ (1 mmol) was charged in the reactor before charging the catalyst mixture.

TABLE 10

| Example | Tm (° C.) | ΔH (J/g) | mmmm (%) | rrrr (%) |
|---|---|---|---|---|
| Ex. 26 | 142.4 | 101 | 90.7 | 0 |
| Ex. 27 | 146.1 | 112 | 92.3 | 0 |
| Ex. 28 | n.d. | n.d. | 0 | 52.6 |

TABLE 11

| Metallocene (g) | Al/Zr (mol) | Yield (g) | Activity (kg/g$_{Zr}$ · h) | η (dl/g) |
|---|---|---|---|---|
| 0.003 | 300 | 130 | 43.3 | 0.27 |
| 0.002 | 500 | 106 | 53.0 | n.d. |
| 0.002 | 1000 | 140 | 70.0 | 0.25 |
| 0.002 | 2800 | 164 | 82.0 | 0.23 |

TABLE 12

| Metallocene (g) | Al/Zr (mol) | T (° C.) | Yield (g) | Activity (Kg/g$_{Zr}$ · h) | η (dl/g) |
|---|---|---|---|---|---|
| 0.002 | 1000 | 30 | 5 | 2.5 | 0.56 |
| 0.002 | 1000 | 40 | 160 | 80.0 | 0.4 |
| 0.002 | 1000 | 50 | 180 | 90.0 | 0.17 |

What is claimed is:

1. A metallocene of formula (I):

$$(ZR^1{}_m)_n(Cp)(A)_rML_pL'_q \qquad (I)$$

wherein $(ZR^1{}_m)_n$ is a divalent group bridging Cp and A, Z is selected from the group consisting of C, Si, Ge, N, or P, and each $R^1$ is independently selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, and $C_7$–$C_{20}$ arylalkyl groups, Cp is a heterocyclic cyclopentadienyl group of formula (IIa), (II'a), (IIb), or (II'b), or Cp is a partially hydrogenated derivative of the heterocyclic group of formula (IIa), (II'a), (IIb), or (II'b):

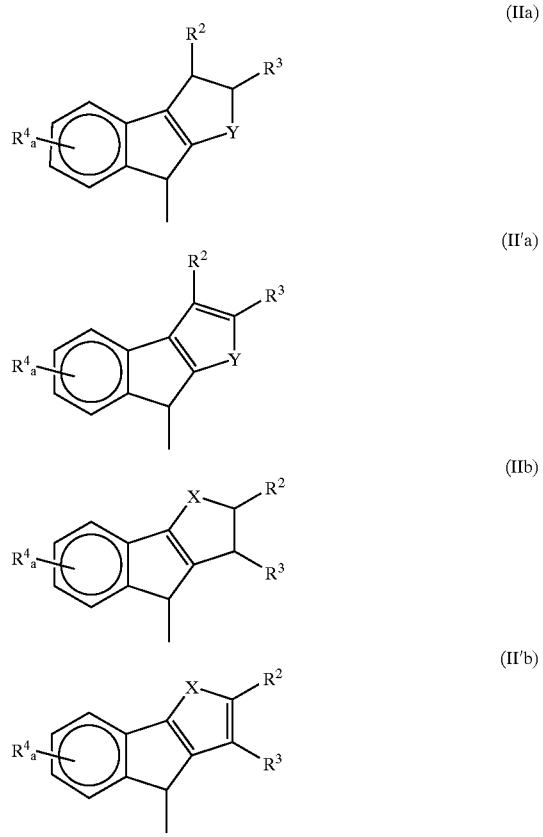

wherein X or Y is selected from the group consisting of O, S, $NR^6$, and $PR^6$ wherein $R^6$ is selected from the group consisting of hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, and $C_7$–$C_{20}$ arylalkyl group, optionally containing one or more atoms belonging to groups 13–16 of the Periodic Table of the Elements;

$R^2$ and $R^3$, the same or different from each other, are selected from the group consisting of hydrogen, halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl, —$OR^6$, —$OCOR^6$, —$SR^6$, —$NR^6{}_2$, wherein $R^6$ has the meaning reported above; or $R^2$ and $R^3$ from together a condensed $C_5$–$C_7$ ring, saturated, unsaturated, or aromatic, optionally containing one or more atoms belonging to groups 13–16 of the Periodic Table of the Elements;

the substituents $R^4$, the same or different from each other, are selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl, $OR^6$, —$OCOR^6$, —$SR^6$, —$NR^6{}_2$, and —$PR^6{}_2$, wherein $R^6$ has the meaning reported above;

a is an integer ranging from 0 to 4;

A is a substitued or unsubstituted cyclopentadienyl, —$NR^6$ wherein $R^6$ has the meaning reported above, corresponds to formula (IIa), (II'a), (IIb), or (II'b), or corresponds to a partially hydrogenated derivative of formula (IIa), (II'a), (IIb), or (II'b);

M is a transition metal belonging to group 3, 4, 5, 6 or to the lanthanide or actinide groups of the Periodic Table of the Elements;

each substituent L is independently a monoanionic sigma ligand selected from the group consisting of hydrogen, halogen, —$R^6$, —$OR^6$, —$OCOR^6$, —$OSO_2CF_3$, —$SR^6$, —$NR^6{}_2$, and $PR^6{}_2$, wherein each $R^6$ group, the same or different from each other, has the meaning reported above;

each substituent L' is independently a Lewis base;

m is 1 or 2, being 1 when Z is N or P, and being 2 when Z is C, Si, or Ge;

n is an integer ranging from 0 to 4; r is 0 when r is 0;

p and q are integers ranging from 0 to 3, p being equal to the valence of the metal M minus when r=1, and minus 1 when r=0, and p+q being $\leq 3$.

2. The metallocene according to claim 1, wherein $(ZR^1{}_m)_n$ is selected from the group consisting of $CR^1{}_2$, $SiR^1{}_2$, $GeR^1{}_2$, $NR^1$, $PR^1$, and $(CR^1{}_2)_2$.

3. The metallocene according to claim 2, wherein $(ZR^1{}_m)_n$ is $SI(CH_3)_2$, $SiPh_2$, $CH_2$, $(CH_2)_2$, or $C(CH_3)_2$.

4. The metallocene according to claim 1, wherein Cp corresponds to formula (IIIa) or formula (IIIb):

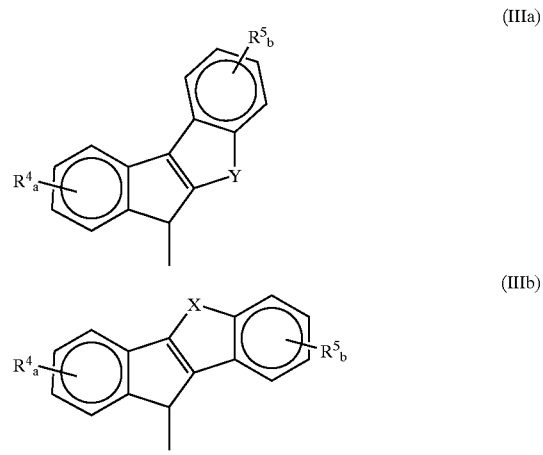

wherein the substituents $R^5$, the same or different from each other, are selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl, —$OR^6$, —$OCOR^6$, —$SR^6$, —$NR^6{}_2$, and —$PR^6{}_2$; and b is an integer ranging from 0 to 4.

5. The metallocence according to claim 4, wherein Cp is selected from the group consisting of 5,10-dihydroindeno [1,2-bi]indol-10-yl, N-methyl-5,10-dihydroindeno [1,2-b]

indol-10-yl, N-phenyl-5,10-dihydroindeno[1,2-b]indol-10-yl, 5,6- dihydroindeno[2,1-b]indol-6-yl, N-methyl-5,6-dihydroindeno[2,1-b]indol-6-yl, N-ally-5,6- dihydroindeno[2,1-b]indol-6-yl, and N-phenyl-5,6-dihydroindeno [2,1-b] indol-6-yl.

6. The metallocene according to claim 4, wherein A corresponds to formula (IIIa) or (IIIb).

7. The metallocene according to claim 6 wherein the metallocene is methylen-bis(N-methyl-5,6-dihydroindeno[2,1-b]indol-6-yl)zirconium dichloride or dimethyl.

8. The metallocene according to claim 1, wherein A is selected from the group consisting of cyclopentadienyl, 4-t-butyl-cyclopentadienyl, 4-adamanthyl-cyclopentadienyl, idenyl, and tetrahydroindenyl.

9. The metallocene according to claim 1, wherein M is Ti, Zr, or Hf.

10. The metallocene according to claim 1, wherein L is halogen or $R^6$.

11. A bridged ligand of formula (IV):

$$(ZR^1{}_m)_n(Cp)(A) \qquad (IV)$$

wherein
$(ZR^1{}_m)_n$ is a divalent group bridging Cp and A, Z is selected from the group consisting of C, Si, Ge, N, and P, and each group is independently selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, and $C_7$–$C_{20}$ arylalkyl groups;

Cp is a heterocyclic cyclopentadienyl group of formula (IIa), (II'a), (IIb), or (II'b), or Cp can be a partially hydrogenated derivative of the heterocyclic group of formula (IIa), (II'a), (IIb), or (II'b):

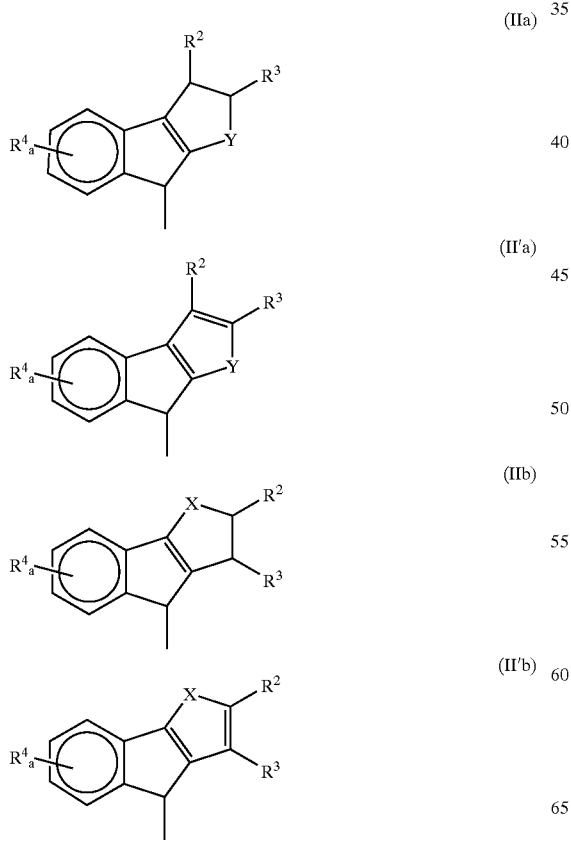

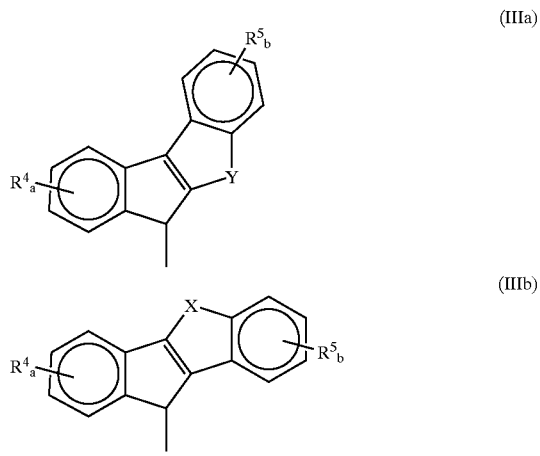

wherein X or Y is selected from the group consisting of O, S, $NR^6$, and $PR^6$ wherein $R^6$ is selected from the group consisting of hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, and $C_7$–$C_{20}$ arylalkyl group, optionally containing one or more atoms belonging to groups 13–16 of the Periodic Table of the Elements;

$R^2$ and $R^3$, the same or different from each other, are selected from the group consisting of hydrogen, halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl, —$OR^6$, —$OCOR^6$, —$SR^6$, —$NR^6{}_2$, and —$PR^6{}_2$, wherein $R^6$ has the meaning reported above; or $R^2$ and $R^3$ can form together a condensed $C^5$–$C^7$ ring, saturated, unsaturated, or aromatic, optionally containing one or more atoms belonging to groups 13–16 of the Periodic Table of the Elements;

the substituents $R^4$, the same or different from each other, are selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl, —$OR^6$, —$OCOR^6$, —$SR^6$, —$NR^6{}_2$, and —$PR^6{}_2$, wherein $R^6$ has the meaning reported above;

a is an integer ranging from 0 to 4;

A is a substituted or unsubstituted cyclopentadienyl, —$NR^6$ wherein $R^6$ having the meaning reported above, corresponds to formula (IIa), (II'a), (IIb), or (II'b), or corresponds to a partially hydrogenated derivative of formula (IIa), (II'a), (IIb), or (II'b);

m is 1 or 2, being 1 when Z is N or P, and being 2 when Z is C, Si, or Ge; and n is an integer ranging from 1 to 4.

12. The bridged ligand according to claim 11, wherein $(ZR^1{}_m)_n$ is selected from the group consisting of $Si(CH_3)_2$, $SiPh_2$, $CH_2$, $(CH_2)_2$, and $C(CH_3)_2$.

13. The bridged ligand according to claim 11, wherein Cp corresponds to formula (IIIa) or (IIIb):

wherein the substituents $R^5$, the same or different from each other, are selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl, —$OR^6$, —$OCOR^6$, —$SR^6$, —$NR^6{}_2$, and —$PR^6{}_2$; and b is an integer ranging from 0 to 4.

14. The bridged ligand according to claim 13, wherein Cp is selected from the group consisting of N-methy-5,10-dihydroindeno[1,2-b]indolyl, N-phenyl-5,10-dihydroindeno[1,2-b]indolyl, N-allyl-5,10-dihydroindeno[1,2-b]indole, N-methyl-5,6-dihydroindeno[2,1-b]indole, N-phenyl-5,6-dihydroindeno[2,1-b]indole, and N-allyl-5,6-dihydroindeno[21,-b]indole.

15. The bridged ligand according to claim 11, wherein A corresponds to formula (IIIa) or (IIIb):

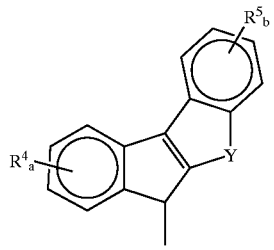

(IIIa)

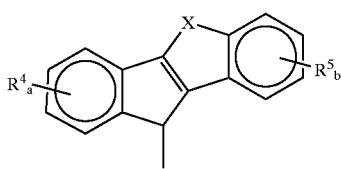

(IIIb)

wherein the substitutes $R^5$, the same or different from each other, are selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl, —$OR^6$, —$OCOR^6$, —$SR^6$, —$NR^6{}_2$, and —$PR^6{}_2$; and b is an integer ranging from 0 to 4.

16. The bridged ligand according to claim 15, wherein the bridged ligand is 6-[N-methyl-5,6-dihydroindeno[2,1-b]indol-6-yl)methyl]-N-methyl-5,6-dihydroindeno[2,1-b]indole.

* * * * *

UNITED STATES PATENT AND TRADEMARK OFFICE
CERTIFICATE OF CORRECTION

PATENT NO.    : 6,451,724 B1
DATED         : September 17, 2002
INVENTOR(S)   : Ilya E. Nifant'ev It is certified that error appears in the above-identified patent and that said Letters Patent is hereby corrected as shown below:

Title page,
Item [57], ABSTRACT,
Line 2, delete the comma before "is".

Column 46,
Line 27, after the second ocurrence of "0", insert -- or 1; n is 0 --.
Line 29, after "minus", insert -- 2 --.
Line 35, change "SI" to -- Si --.

Column 47,
Line 3, change "ally" to -- allyl --.
Line 26, after "each", insert -- $R^1$ --.

Column 49,
Line 7, change "21," to -- 2,1 --.

Column 50,
Line 10, change "substitutes" to -- substituents --.

Signed and Sealed this

Thirteenth Day of May, 2003

JAMES E. ROGAN
*Director of the United States Patent and Trademark Office*